United States Patent

Bach et al.

[11] Patent Number: 5,807,866
[45] Date of Patent: Sep. 15, 1998

[54] PROCESS FOR PREPARING N-BENZYL INDOLES

[75] Inventors: Nicholas James Bach, Indianapolis, Ind.; Stephen Richard Baker; Jeremy Gilmore, both of Surrey, United Kingdom; Russell Andrew Lewthwaite, Cambridge, United Kingdom; Alexander McKillop, Norwich, United Kingdom; Jason Scott Sawyer, Indianapolis, Ind.; George Richard Stephenson, Norwich; Michael William John Urquhart, Kent, both of United Kingdom

[73] Assignees: The University of East Anglia, Norwich, United Kingdom; Eli Lilly and Company, Indianapolis, Ind.

[21] Appl. No.: 753,024

[22] Filed: Nov. 19, 1996

[30] Foreign Application Priority Data

Nov. 23, 1995 [GB] United Kingdom ............ 9523948

[51] Int. Cl.[6] ................ C07D 241/00; C07D 401/10; C07D 401/12; A61K 31/47

[52] U.S. Cl. .............. 544/284; 544/353; 546/174; 546/175; 546/176; 546/177; 546/273; 548/159; 548/548; 548/181; 548/217; 514/249; 514/259; 514/314; 514/339; 514/365; 514/367; 514/374

[58] Field of Search ................ 544/284, 353; 546/174–177, 273; 548/159, 181, 217; 514/249, 365, 259, 367, 314, 374, 339

[56] References Cited

U.S. PATENT DOCUMENTS

| | | | |
|---|---|---|---|
| 4,471,130 | 9/1984 | Katsuki et al. | 549/523 |
| 4,900,847 | 2/1990 | Hanson et al. | 549/529 |
| 5,281,593 | 1/1994 | Gilmore et al. | 514/249 |

FOREIGN PATENT DOCUMENTS 0 469 833  5/1992  European Pat. Off. ...... C07D 401/14

OTHER PUBLICATIONS

Raner et al., Aust. J. Chem., 1990, 43, 609–16.
JP 56147768, CA 96:122633, CAS Online Printout.
Farmaco Ed. Sci., vol. 21, No. 3, 1966, pp. 209–215, XP000651099 M.F. Saettone: "Sintesi di alcuni monocarbammati derivati dall'eritro–3–amino–3–fenil–1,2–propandiolo".
J. Heterocycle. Chem., vol. 23, No. 5, 1986, pp. 1599–1602, XP000651131, D. Badia, et al., "Synthesis and Stereochemistry of Tetrahydroprotoberberine Derivatives".
J. Heterocycl. Chem., vol. 20, No. 2, 1983, pp. 295–299, XP000651136, M.P. Lamontagne, "Preparation of 7–substituted pyrrolo [2,3–d] pyrimidines and 9–substituted purines as potential antiparasitic agents".
Tetrahedron Lett., vol. 32, No. 47, 1991, pp. 6931–6934, XP000651140, M. Canas, et al., "Regioselective ring opening of chiral epoxyalcohols by primary amines".

Primary Examiner—S. Mark Clardy
Assistant Examiner—Sabiha N. Qazi
Attorney, Agent, or Firm—Brian P. Barrett; David E. Boone

[57] ABSTRACT

A process for producing a compound of the formu5la

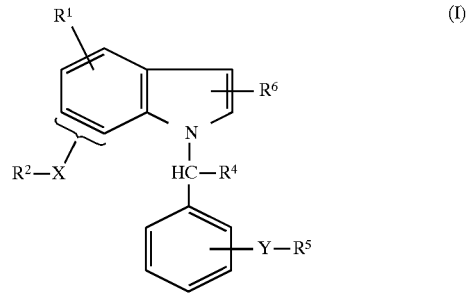

comprising the step of reacting a compound of the formula

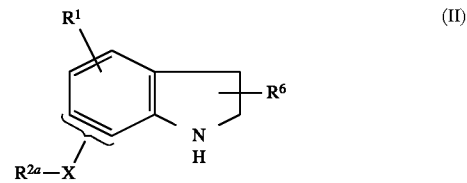

with a compound of the formula

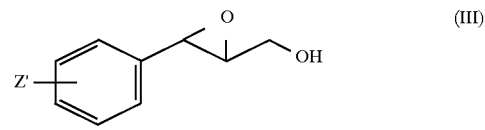

to form a compound of the formula

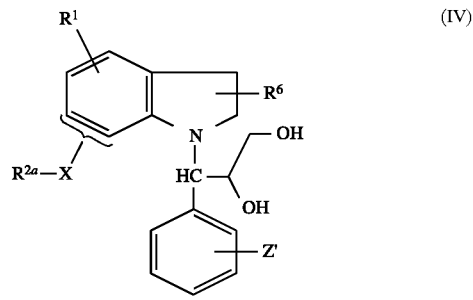

wherein $R^{2a}$ is selected from the groups recited above for $R^2$, or $R^{2a}$—X— is a protected hydroxyl group, and Z is a group of formula —Y—$R_5$ recited above, or a group that can be converted into a group of said formula —Y—$R^5$. Intermediates of formula IV and composition containing substantially optically pure enantiomers of Formula (I) are included within the scope of the invention.

19 Claims, No Drawings

PROCESS FOR PREPARING N-BENZYL INDOLES

This invention relates to a process for the preparation of N-benzyl indoles, and to intermediates for use in the process, and to certain substantially optically pure N-benzyl indoles obtained by the process.

EP-A-0469833 discloses a class of N-benzyl indoles including compounds of the formula

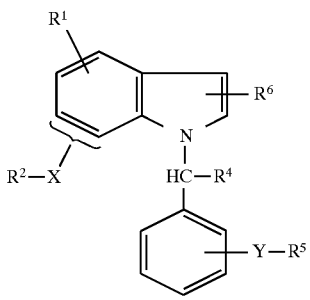

(I)

in which $R^1$ is hydrogen, halo, $C_{1-4}$ alkyl, $C_{1-4}$ alkoxy, nitrile, optionally protected carboxy, optionally protected tetrazolyl, trihalomethyl, hydroxy-$C_{1-4}$ alkyl, aldehyde, —$CH_2Z$, —$CH=CH-Z$ or —$CH_2CH_2Z$ where Z is optionally protected carboxy or optionally protected tetrazolyl; $R^2$ is halo, nitrile, an optionally protected acid group or —$CONR^7R^8$ where $R^7$ and $R^8$ are hydrogen or $C_{1-4}$ alkyl; $R^4$ is $C_{2-4}$ alkyl, or $C_{2-4}$ alkyl substituted by —$CONR^7R^8$ or an optionally protected acid group; $R^5$ is

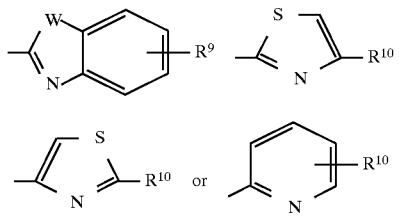

where W is —CH=CH—, —CH=N—, —N=CH—, —O— or —S—, $R^9$ is hydrogen, halo, $C_{1-4}$ alkyl, $C_{1-4}$ alkoxy or trihalomethyl, and $R^{10}$ is hydrogen, $C_{1-4}$ alkyl, $C_{2-6}$ alkenyl, $C_{3-6}$ cycloalkyl or $C_{1-4}$ alkyl-$C_{3-6}$ cycloalkyl; $R^6$ is hydrogen or $C_{1-4}$ alkyl; X is —O—$(CH_2)_n$$CR^{11}R^{12}$—, —$CR^{11}R^{12}$—, —$CR^{11}R^{12}.(CH_2)_n.CR^{13}R^{14}$— or —$CR^{11}=CR^{12}$— where $R^{11}$, $R^{12}$, $R^{13}$ and $R^{14}$ are each hydrogen or $C_{1-4}$ alkyl, and n is 0, 1 or 2; and Y is —O—$CR^{15}R^{16}$—, —$CR^{15}=CR^{16}$— or —$CR^{15}R^{16}.CR^{17}R^{18}$— where $R^{15}$, $R^{16}$, $R^{17}$ and $R^{18}$ are each hydrogen or $C_{1-4}$ alkyl; and salts thereof.

Among the compounds disclosed in EP-A-0469833, one particularly important compound has the formula

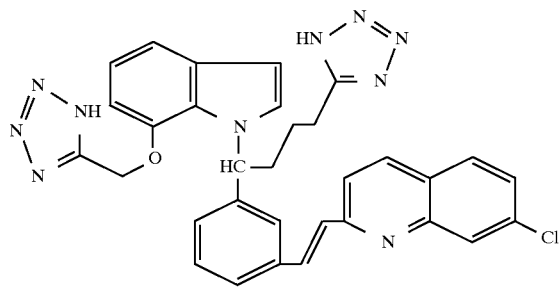

(I')

The compounds disclosed in EP-A-0469833 are leukotriene antagonists, and are accordingly indicated for therapeutic use in the treatment of diseases in which leukotrienes are implicated. These include allergic reactions of the pulmonary system in which leukotrienes are thought to be causal mediators of bronchospasm, for example, in allergic lung disorders such as extrinsic asthma and industrial asthmas such as Farmers Lung, and in other inflammatory disorders, for example, associated with acute or chronic infectious diseases such as allergic skin diseases, ectopic and atopic eczemas, psoriasis, contact hypersensitivity and angioneurotic oedema, bronchitis and cystic fibrosis and rheumatic fever. The compounds disclosed in EP-A-0469833 also have potential in the treatment of vascular diseases such as shock and ischemic heart diseases for example coronary artery disease and myocardial infarction, cerebrovascular diseases, and renal diseases such as renal ischemic.

EP-A-0469833 discloses certain processes for the preparation of the N-benzyl indoles disclosed therein. However, the overall yield which is obtainable using the processes disclosed in EP-A-0469833 is not high, and the compounds are generally obtained in the form of racemates. In many cases, including the case of the compound of Formula (I') above, separation of enantiomers by conventional techniques, such as by reaction with a chiral amine followed by fractional recrystallisation, or separation on a chiral chromatographic support has been found to be extremely difficult. Nevertheless it has now been found that the S-enantiomer of the above compound of Formula (I') is preferred and pharmacologically superior.

It is accordingly an object of the present invention to provide an improved process for preparing the N-benzyl indoles described above. It is a further object of the invention to provide a process for preparing such N-benzyl indoles in the form of their substantially pure enantiomers.

According to one aspect of the present invention, there is provided a process which comprises the step of reacting an indoline compound of the formula

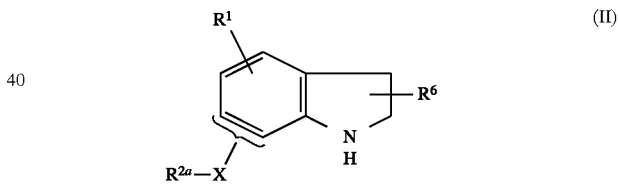

(II)

with epoxide compound of the formula

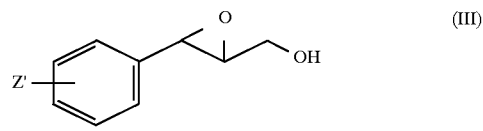

(III)

to form a compound of the formula

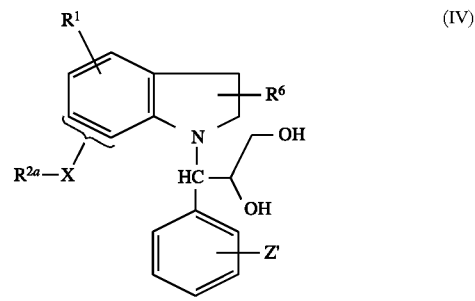

(IV)

wherein $R^{2a}$ is selected from the groups recited above for $R^2$, or $R^{2a}$—X— is a protected hydroxyl group, and wherein Z' is a group of formula —Y—$R^5$ as defined herein, or Z' is a substituent that can be converted into a group of formula —Y—$R^5$. In any event, the group W must be chemically stable during the above-described reaction between compounds of formulae (II) and (III). Since the linking group Y is preferably a vinyl group —$CR^{15}$=$CR^{16}$—, the substituent Z' is preferably a group that can be converted into a vinyl group by an olefination reaction. The preferred olefination method is palladium salt catalyzed Heck coupling, as described further below, and accordingly Z' is preferably a leaving group such as Cl, Br, I, or a sulfonate such as trifluoromethylsulfonate or tosylate. The most preferred substituent Z' in this case is Br. Other preferred olefinations include Wittig reactions, in which case the substituent Z' is preferably —CHO, or protected —CHO, such as an acetal.

The reaction is carried out in a suitable solvent such as dry acetonitrile, and is preferably conducted in the presence of a Lewis acid catalyst such as magnesium perchlorate.

In the above formula (I), a halo substituent can be for example, chloro, bromo and fluoro and is preferably chloro. A $C_{1-4}$ alkyl group includes methyl, ethyl, propyl, isopropyl, butyl and tert butyl and is preferably methyl or ethyl, and a $C_{1-4}$ alkoxy group is one such alkyl group attached through oxygen. A hydroxy $C_{1-4}$ alkyl group is a hydroxy-substituted $C_{1-4}$ alkyl group preferably of the formula $HO(CH_2)_n$— where n is 1 to 4, a preferred example being hydroxymethyl. A $C_{3-6}$ cycloalkyl group includes for example cyclopropyl, cyclopentyl and cyclohexyl, and is preferably cyclopropyl. The $C_{3-6}$ cycloalkyl group can be substituted by a $C_{1-4}$ alkyl. A $C_{2-6}$ alkenyl group is preferably propenyl or isopropenyl. A trihalomethyl group is preferably trifluoromethyl. An optionally substituted phenyl group is phenyl itself, or phenyl substituted with one or more, preferably 1 to 3, substituents selected from $C_{1-4}$ alkyl, especially methyl, $C_{1-4}$ alkoxy, especially methoxy and ethoxy, hydroxy, nitro, cyano, halo, especially chloro or fluoro, trihalomethyl, especially trifluoromethyl, carboxy $C_{1-4}$ alkoxy-carbonyl, and optionally protected tetrazolyl.

An acid group can be any acid group conventionally used in pharmaceutical chemistry and the term includes, for example tetrazolyl (1H-tetrazol-5-yl), carboxy (—COOH), phosphonate (—PO(OH)$_2$), sulphonate (—SO$_2$OH), acyl sulphonamido (—CONHSO$_2$R, where R is preferably $C_{1-4}$ alkyl or optionally substituted phenyl) or cyanoguanidinyl (—NHC(NH$_2$)=NCN). Especially preferred examples are tetrazolyl and carboxy.

When $R^5$ is the group

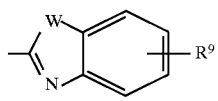

it comprises groups of the following type

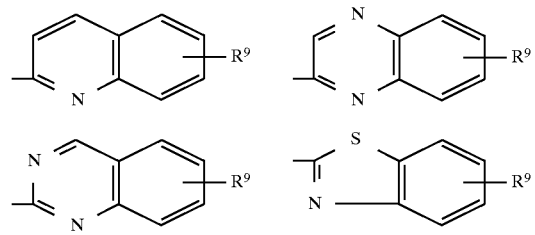

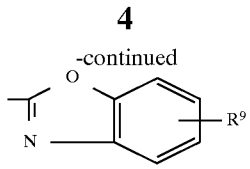

and the quinolin-2-yl group is the most preferred.

$R_1$ is preferably hydrogen or halogen, and especially hydrogen, and when it is other than hydrogen it is preferably attached to the indole nucleus at the 4-position.

The group $R^2$—X— is attached to the indole nucleus at the 6- or 7-position, and when X is —O—$(CH_2)_n$$CR^{11}CR^{12}$— via the oxygen atom. $R^2$ is preferably an acid group especially tetrazolyl or carboxyl.

The $R^5$ group is preferably quinolin-2-yl where the substituent $R^9$, which is preferably hydrogen or halo, is attached at the 7-position. The group $R^5$—Y— can be attached with the 2-, 3- or 4- positions to the phenyl nucleus, and when R is —O—$CR^{15}R^{16}$— via the oxygen atom. $R^5$—Y— is preferably attached at the 3-position.

The $R^6$ group is preferably hydrogen and when it is $C_{1-4}$ alkyl is preferably attached at the 3-position.

The linking group X is preferably —O—$CR^{11}R^{12}$— or $CR^{11}R^{12}.CR^{13}R^{14}$—, and $R^{11}$, $R^{12}$, $R^{13}$ and $R^{14}$ are preferably hydrogen. Linking group Y is preferably of the formula —O—$CR^{15}R^{16}$, or —$CR^{15}$=$CR^{16}$—, and $R^{15}$, $R^{16}$, $R^{17}$, and $R^{18}$ are preferably hydrogen.

When acid substituents on the compound of formula (I) require protection during preparation they may be protected by conventional protecting groups. Such protected compounds are included in the scope of the invention, though the preferred compounds with optimum biological properties are the unprotected compounds derived from them. A carboxy can be protected by protecting groups which include the well known ester forming groups used for the temporary protection of acidic carboxylic acid groups. Examples of such groups which have general use are readily hydrolyzable groups such as arylmethyl groups, haloalkyl groups, trialkylsilyl groups, alkyl groups, and alkenyl groups. A preferred protected carboxy is $C_{1-4}$ alkoxy-carbonyl. Other carboxy protecting groups are described by E. Haslam in *Protective Groups in Organic Chemistry*. Such protecting groups are also suitable for protecting phosphonate and sulphonate substituents. Furthermore, it is usually necessary to protect any tetrazolyl group during the process of preparation, and suitable and well known protecting groups for this purpose include groups of the formula —CR'R"R'" where R' and R" are hydrogen, $C_{1-4}$ alkyl or phenyl optionally substituted by one or more electron-donating groups such as, for example, $C_{1-4}$ alkoxy, and R'" is phenyl optionally substituted by one or more electron donating groups. Preferred examples include trityl and benzhydryl.

When the acid substituent is tetrazolyl, then most preferred methods involve carrying out the earlier reaction steps on precursor nitrile compounds, and then converting the nitrile groups into tetrazolyl by reaction with an azide at or near the last step of the synthesis.

It is believed that all of the other substituents defined herein for compounds of formula (I) may be present when compound (II) is reacted with compound (III) in accordance with the present invention, and the substituents should not substantially interfere with this reaction step. It will be recognized that side reactions may occur with certain substituents in certain of the other reaction steps in the preferred total synthesis route described herein. The person skilled in the art will recognize where side reactions could occur and avoid the side reactions by means of suitable protecting groups, or the like.

The compounds of Formula IV as defined above form a further aspect of the present invention.

Preferably, the process according to the present invention further comprises the step of converting the compound of formula IV into a compound of formula (IVa)

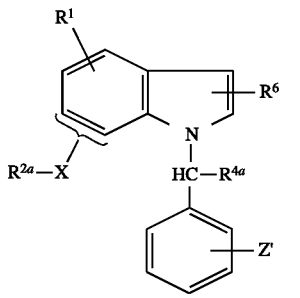

(IVa)

where $R^{4a}$ is $C_{2-4}$ alkyl or $C_{2-4}$ alkyl substituted by cyano, hydroxy, —$CONR^7R^8$, or an optionally protected acid group.

For example, the present invention preferably provides a process as above for preparing a compound of formula (I), further including the step of converting the compound of formula (IV) to the olefin

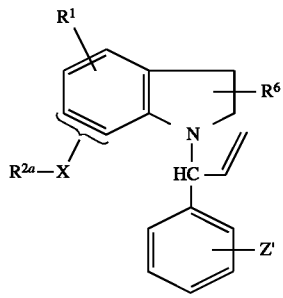

(V)

The compound of formula (IV) may be converted into the olefin via the thiocarbonate (Va)

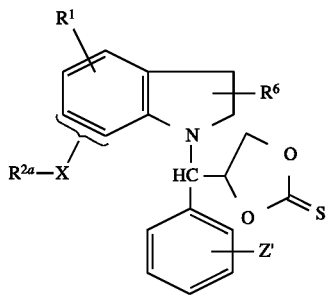

using the Corey-Winter olefination method. For example, 1,1'-thiocarbonyldiimidazole and 4-dimethylaminopyridine in dichloromethane may be used to obtain the thiocarbonate, and a trivalent phosphorus reagent such as 1,3-dimethyl-2-phenyl1,3,2-diazaphospholidine is then used to convert the thiocarbonate to the olefin. This reaction is preferably carried out in a solvent such as THF.

The olefin of Formula (V), in turn, is preferably converted to the corresponding alcohol (VI)

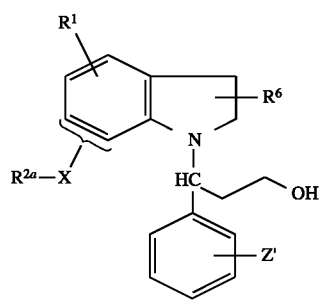

(VI)

by a hydroboration-oxidation sequence, such as heating with borane-tetrahydrofuran complex ($BH_3$—THF) in tetrahydrofuran, followed by the addition of water, alkali metal hydroxide and hydrogen peroxide.

Preferably, the method of the present invention then includes the step of oxidizing the above indoline alcohol compound to the corresponding indole compound of the formula

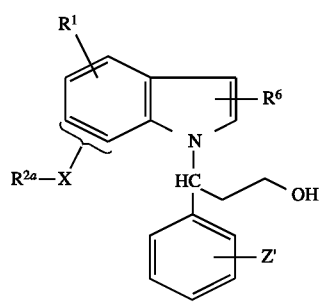

(VII)

Such oxidation may conveniently be achieved by reaction with chlorotrimethylsilane and triethylamine in dichloromethane, followed by treatment with a mild oxidizing agent, such as 2,3-dichloro-5,6-dicyano-1,4-benzoquinone (DDQ).

Preferably, the indole alcohol of formula (VII) is then converted into a compound of formula (IVa)

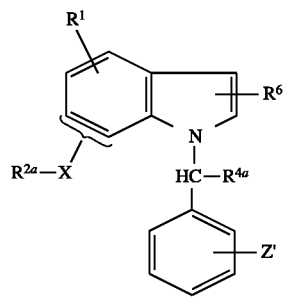

This step is preferably carried out by: (i) converting the hydroxyl group into an anionic leaving group, e.g. converting the hydroxyl group into trifluoromethylsulfonate by treatment with trifluoromethylsulfonic anhydride and mild base, followed by (ii) reaction with a suitable nucleophile to produce the desired group $R^{4a}$, e.g. reaction with cyanide ion, or cyanomethylation with $NCCH_2CO_2H$ and lithium diisopropylamide, or with $CH_3CN$ and lithium diisopropylamide in aprotic solvent.

When $R^{2a}$—X— is a protected hydroxy group, the process according to the invention may further comprise the step of removing the protecting group $R^{2a}$ from the compound of formula (VII) and then reacting the deprotected compound with a compound of the formula Br—(CH$_2$)$_n$CR$^{11}$R$^{12}$—R$^2$, wherein n, R$^{11}$ and R$^{12}$ are as defined above, to form a compound of the formula

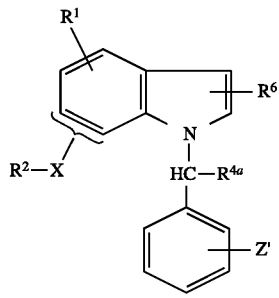
(VIII)

The protecting group R$^{2a}$ may conveniently be removed using a conventional O-dealkylating agent, such as boron tribromide in a solvent such as dichloromethane.

In preferred embodiments, the present invention provides a process for preparing a compound of formula (I), wherein Y is —CR$^{15}$=CR$^{16}$—, comprising the step of reacting the compound of formula (IVa) wherein Z' is an anionic leaving group, preferably Br, with a compound of the formula CHR$^{15}$=CR$^{16}$—R$^5$ in a Heck coupling reaction to form a compound of the formula

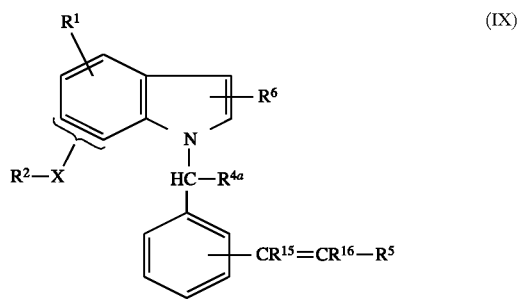
(IX)

The Heck coupling reaction requires the presence of a palladium salt as catalyst, a polar solvent, a base, and a monodentate or bidentate phosphine ligand. For example, the reaction preferably uses bisdiphenylphosphinopropane, palladium dichloride in acetonitrile and triethylamine. It has been found that, for compounds of formula VIII, the reaction can be carried out in a sealed bottle at a temperature of 90° to 100° C.

When R$^{2a}$, in formula (IX) is cyano and/or R$^{4a}$ is cyano-C$_{2-4}$ alkyl, the compound of formula (IX) may be reacted with an azide, such as Bu$_3$SnN$_3$, to convert the cyano groups to tetrazolyl groups.

Preferably, the compound of formula (III) is formed by epoxidation of a compound of the formula

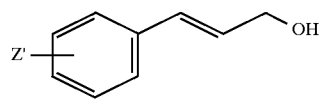

The epoxidation is preferably a Sharpless asymmetric epoxidation, as described in U.S. Pat. No. 4,471,130 or U.S. Pat. No. 4,900,847, the entire disclosure of which is incorporated herein by reference. This epoxidation is carried out with a titanium alkoxide, an organic hydroperoxide, and a chiral glycol in an inert aprotic solvent. Preferred reagents are Ti(O$^i$Pr)$_4$, t-BuOOH and diethyl tartrate. If the diethyl tartrate is the L-(+)-isomer, then the resulting compound of formula (III) has the structure

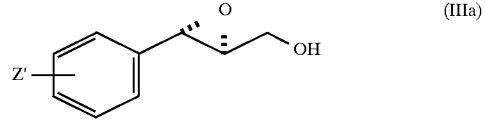
(IIIa)

and the resulting compound of formula (I) has the structure

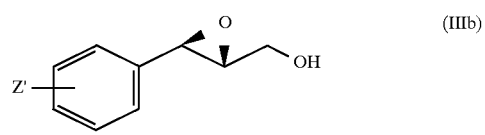
(Ia)

On the other hand, if the diethyl tartrate is the D-(−)-isomer, then the resulting compound of formula (III) has the structure

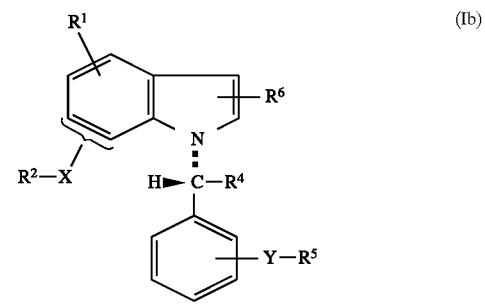
(IIIb)

and the resulting compound of formula (I) has the structure

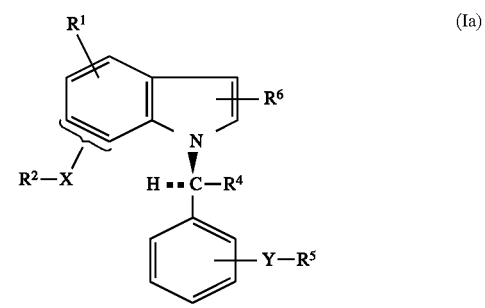
(Ib)

Accordingly, the present invention also provides compositions comprising a compound of formula (Ia)

substantially free of the enantiomer

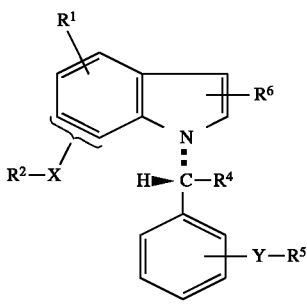
(Ib)

as well as compositions comprising a compound of formula (Ib) substantially free of the enantiomer (Ia). The enantiomeric ratio in such compositions is preferably at least 80:10, and more preferably at least 90:10. In many cases, an enantiomeric ratio greater than 95:5 is obtained.

The invention is now illustrated by the following examples, which describe the synthesis of the two enantiomers of formula (Ia) and (Ib) above, including the synthesis of intermediates according to the present invention:

PROCEDURE I

Synthesis of 7-chloro-2-ethenylquinoline (a) 2-Bromomethyl-7-chloroquinoline

A solution of diisopropylamine (3.6 ml, 24.86 mmol) in dry tetrahydrofuran (25.0 ml) at −20° C. under nitrogen was treated with a 2.5M solution of n-butyllithium in hexane (10.0 ml, 24.86 mmol). This lithium diisopropylamide solution was stirred below −10° C. for 30 min and 7-chloroquinaldine (4.0 g, 22.6 mmol) was added in portions. The resulting dark red solution was stirred at −10° C., increasing to 0° C. for 1 h, cooled to −30° C. and treated with chlorotrimethylsilane (4.4 ml, 33.92 mol) dropwise to return a golden yellow solution. After stirring below −20° C. for 2 h a solution of bromine (1.2 ml, 22.6 mmol) in tetrahydrofuran (25.0 ml) was added dropwise over a 30 min period maintaining an addition temperature of below −20° C. at all times. The mixture was stirred below −20° C. for 1 h, quenched with water (300 ml), extracted into ethyl acetate (3×100 ml), the combined organic extracts were washed with saturated ammonium chloride solution (2×200 ml), dried (Na$_2$SO$_4$) and evaporation of the solvent afforded a brown oily solid. Column chromatography (ethyl acetate—light petroleum (b.p. 40°–60° C.), 1:4) gave the title compound (3.62 g, 76%) as a yellow solid. Crystallised from light petroleum (b.p. 40°–60° C.) as white crystals, m.p. 108°–112° C. (lit. m.p. 112° C. (dec.)). ν$_{max}$ (nujol)/cm$^{-1}$ 1593.5, 1559.5. δH (270 MHz) 4.68 (2H, s, C$\underline{H}_2$Br); 7.50 (1H, dd, 6-H, J$_o$=8.6, J$_m$=2.0 Hz); 7.56 (1H, d, 3-H, J$_o$=8.3 Hz); 7.74 (1H, d, 5-H, J$_o$=8.9 Hz); 8.06 (1H, d, 8-H, J$_m$=2.0 Hz); 8.14 (1H, d, 4-H, J$_o$=8.6 Hz). δ$_C$(67.8 MHz) 34.0 ($\underline{C}H_2$Br), 121.4 (3-C), 125.6 (4a-C), 135.9 (8a-C), 137.1 (4-C), 158.0 (2-C). Remaining signals fall in the narrow range 128.0–128.3 ppm.

(b) (7-Chloroquinolin-2-yl)methyltriphenylphosphonium bromide

Triphenylphosphine (1.83 g, 6.99 mmol) was added portionwise to a magnetically stirred solution of 2-bromomethyl-7-chloroquinoline (1.2 g, 4.69 mmol) in dry acetonitrile (10.0 ml) at 60° C. The resulting yellow solution was heated at 60° C. for 27 h with the precipitation of a cream solid. The cooled solution was diluted with diethyl ether (8.0 ml) and filtered to afford the title compound as a cream solid (1.95 g, 80%). Crystallised from ethanol and ethyl acetate as a cream microcrystalline solid, m.p. >200° C.; (Found: C, 64.61; H, 4.22; N, 2.62; Cl, 6.82. C$_{28}$H$_{22}$ClBrNP requires C, 64.82; H, 4.27; N, 2.70; Cl, 6.83%). ν$_{max}$ (nujol)/cm$^{-1}$ 1610.0, 1594.0. δH (270 MHz) 5.94 (2H, d, C$\underline{H}_2$P, $^3$J=14.2 Hz); 7.43 (1H, dd, 6-H, J$_o$=8.6, J$_m$=2.0 Hz); 7.50 (1H, d, 8-H, J$_m$=2.0 Hz); 7.57–7.95 (16H, m, ArH); 8.03 (1H, d, 3-H, J$_o$=8.6 Hz); 8.11 (1H, d, 4-H, J$_o$=8.6 Hz); m/z 437.4 (1.18), 262.3 (11.01), 177.1 (3.13), 43.1 (100).

(c) Diethyl 7-chloro-2-quinolylmethylphosphonate
Method 1

A magnetically stirred solution of 2-bromomethyl-7-chloroquinoline (1.0 g, 3.91 mmol) and triethyl phosphite (0.74 g, 4.45 mmol) in dry toluene (10.0 ml) was heated under reflux for 24 h. The cooled solution was adsorbed onto a quantity of silica (ca. 5.0 g) and column chromatography (ethyl acetate—light petroleum (b.p. 40°–60° C.), 1:4) provided unreacted 2-bromomethylquinoline (0.12 g, 0.469 mmol—12%) as brown crystals. Further elution (ethyl acetate) secured the title compound (0.88 g, 72%) as a yellow / brown oil. Distilled at 240° C. at 0.05 mmHg using a Kugelrohr short-path distillation apparatus as a bright yellow oil which crystallised on standing (m.p. 33°–37° C.); (Found: C, 53.17; H, 5.40; N; 4.31; Cl, 11.22. C$_{14}$H$_{17}$ClNO$_3$P requires C, 53.6; H, 5.46; N, 4.46; Cl, 11.3%); ν$^{max}$ (thin film)/cm$^{-1}$ 3060.5, 2981.5, 1612.5, 1598.5, 1559.5. δ$_H$ (270 MHz) 1.27 (6H, t, 2×CH$_2$C$\underline{H}_3$, $^3$J=6.9 Hz); 3.60 (2H, d, C$\underline{H}_2$P, $^2$J=22.4 Hz); 4.11 (4H, m, 2×C$\underline{H}_2$CH$_3$); 7.47 (1H, dd, 3-H, J$_o$=7.0, $^4$J$_{3H,P}$=0.8 Hz); 7.51 (1H, dd, 6-H, J$_o$=8.4, J$_m$=1.5 Hz); 7.72 (1H, d, 5-H, J$_o$=8.9 Hz); 8.05 (1H, d, 8-H, J$_m$=1.7 Hz); 8.06 (1H, d, 4-H, J$_o$=8.3 Hz). δ$_C$ (67.8 MHz) 16.15 (CH$_2$$\underline{C}$H$_3$, d, $^3$J$_{C,P}$=6.1 Hz); 37.0 ($\underline{C}$H$_2$P, d, $^1$J$_{C,P}$=134.3 Hz); 62.3 ($\underline{C}$H$_2$CH$_3$, d, $^2$J$_{C,P}$=6.1 Hz); 122.3 (3-C, d, $^3$J$_{C,P}$=2.5 Hz), 125.1 (4a-C), 135.3 (7-C), 136.2 (4-C); 147.9 (8a-C), 154.3 (2-C, d, $^2$J$_{C,P}$=8.6 Hz). Remaining signals fall in the narrow range 127.1–128.6 ppm; m/z 315.3, 313.2 (7.52, 22.18, M$^+$), 277.3 (2.21), 242.1, 240.1 (1.79, 5.13), 193.1 (6.84), 179.1, 177.1 (33.1, 100), 142.2 (3.65), 109.1 (4.57).

Method 2

A 2.5M solution of n-butyllithium in hexane (25.0 ml, 62.15 mmol) was added dropwise to a magnetically stirred solution of diisopropylamine (9.0 ml, 62.15 mmol) in tetrahydrofuran (80.0 ml) at −20° C. under nitrogen. The resulting pale yellow solution was stirred below −10° C. for 30 min and treated with 7-chloroquinaldine (10.0 g, 56.5 mmol) in portions. The solution of the dark red anion was stirred below −5° C. for 1 h then cooled to −20° C. and treated dropwise with a solution of diethyl chlorophosphate (9.0 ml, 62.3 mmol) in tetrahydrofuran (20.0 ml). Stirred below 0° C. for 1 h, recooled to −20° C. and treated dropwise with a further quantity of lithium diisopropylamide (62.15 mmol). This dark grey mixture was allowed to warm to 0° C. over 20 min then quenched with water (500 ml), extracted into ethyl acetate (3×200 ml), the combined organic extracts were washed with brine (2×200 ml), dried (Na$_2$SO$_4$) and evaporated to provide an orange/brown oil. Column chromatography (ethyl acetate—light petroleum (b.p. 40°–60° C.), 7:3) provided the title compound as an orange solid (12.6 g, 71%) whose physical and spectroscopic properties were identical to those described above.

(d) 7-Chloro-2-ethenylquinoline

A stirred solution of diisopropylamine (2.24 ml, 15.97 mmol) in tetrahydrofuran (15.0 ml) at −10° C. under nitrogen was treated dropwise with a 2.5M solution of n-butyllithium in hexane (6.4 ml, 15.97 mmol). After stirring below 0° C. for 30 min the pale yellow solution was cooled to −20° C. and a solution of diethyl 7-chloro-2- quinolylmethylphosphonate (5.0 g, 15.97 mmol) in tetrahydrofuran was added dropwise. The resulting dark green solution was stirred below 0° C. for 1 h, cooled to −10° C. and treated with paraformaldehyde (0.53 g, 17.57 mmol) in portions. Stirred cold for 15 min after which the cooling bath was removed and the mixture was stirred at 25° C. for 90 min. Quenched with brine (300 ml), extracted into ethyl acetate (3×100 ml), the combined organic extracts were washed with brine (3×200 ml), dried ($Na_2SO_4$) and the solvent was removed in vacuo to give a dark brown solid. Column chromatography (ethyl acetate—light petroleum (b.p. 40°–60° C.), 1:19) provided the title compound (1.80 g, 59%) as pale yellow crystals. Crystallised from ethyl acetate and light petroleum (b.p. 40°–60° C.) as cream crystals, m.p. 79.7°–80° C. (Found: C, 69.84; H, 4.15; N; 7.25; Cl, 18.91. $C_{11}H_8ClN$ requires C, 69.67; H, 4.25; N, 7.39; Cl, 18.69%); $v_{max}$ (nujol) /cm$^{-1}$ 1628, 160; $\delta_H$ (270 MHz) 5.67 (1H, dd, 2'-H, $^3J_{2',1''}$=10.89, $^2J_{2'',2''}$=1.0 Hz); 6.29 (1H, dd, 2"-H, $^3J_{2'',1''}$=17.7, $^2J_{2'',2''}$=0.8 Hz); 7.02 (1H, dd, 1'-H, $^3J_{1',2''}$=17.5, $^3J_{1',2'}$=10.9 Hz); 7.42 (1H, dd, 7-H, $J_o$=8.8, $J_m$=2.1 Hz); 7.53 (1H, d, 3-H, $J_o$,8.9 Hz); 7.66 (1H, d, 5-H, $J_o$=8.9 Hz); 8.03 (1H, d, 4-H, $J_o$=8.3 Hz); 8.05 (1H, s, 8-H). $\delta_C$ (67.8 MHz) 118.6 (2'-C); 120.5 (3-C); 125.7 (4a-C); 135.3 (7-C); 136.0 (4-C); 137.5 (1'-C); 148.3 (8a-C); 156.9 (2-C). Remaining signals fall in the range 127.1–128.5 ppm; m/z 191.0, 189.0 (33.48, 100, M$^+$), 165.0, 163.0 (21.89, 65.87), 154.0 (5.13), 128.1 (9.14).

PROCEDURE 2

Synthesis of 7-Benzyloxyindoline (a) 7-Benzyloxyindoline

A magnetically stirred solution of 7-benzyloxyindole (16.0 g, 71.66 mmol) in glacial acetic acid (200 ml) at 10° C. under nitrogen was treated with sodium cyanoborohydride (10.0 g, 0.159 mol) in portions via a powder funnel maintaining an addition temperature of below 17° C. Resulting white suspension was stirred below 20° C. for 4 h and quenched with water (300 ml). Evaporation in vacuo gave a colorless oil which was diluted with ethyl acetate (300 ml) treated with 2M sodium hydroxide (400 ml) and stirred vigorously for 16 h. The organic layer was separated, the aqueous was extracted with ethyl acetate (3×100 ml), the combined organic phases were washed with aqueous 2M $NaOH_{(aq)}$ (200 ml) brine (2×200ml), dried ($Na_2SO_4$) and evaporation of the solvent gave the crude product as an oily white solid. Column chromatography (ethyl acetate—light petroleum (b.p. 40°–60° C.), 1:9) provided the title compound (14.1 g, 89%) as white crystals. Crystallised from ethyl acetate and light petroleum (b.p. 40°–60° C.) as colourless plates (m.p. 58°–60° C.). (Found: C, 80.04; H, 6.58; N; 6.19. $C_{15}H_{15}NO$ requires C, 79.97; H, 6.71; N, 6.22%); $v_{max}$ (nujol)/cm$^{-1}$ 3332, 30338, 1885, 1618, 1591; $\delta_H$ (270 MHz) 3.02 (2H, 2×2-H, $^3J_{2,3}$=8.4 Hz); 3.51 (2H, 2×3-H, $^3J_{3,2}$=8.6 Hz); 3.80 (1H, bs, N-H); 5.02 (2H, s, C$\underline{H}_2$Ph); 6.65 (2H, m, 4-H, 5-H); 6.80 (1H, m, 6-H); 7.33 (5H, m, Ph). $\delta_C$ (67.8 MHz) 30.3 (2-C); 47.62 (3-C); 70.1 (O$\underline{C}H_2$Ph); 110.8 (6-C); 117.5 (5-C); 118.9 (4-C); 130.4 (3a-C); 137.2 (7a-C); 140.9 (benzyl ipso-C); 144.4 (7-C). Remaining signals lie between 127.3–128.4 ppm; m/z 225.2 (17.24, M$^+$), 134.1 (100), 116.1 (14.06), 91.1 (29.15).

PROCEDURE 3

Synthesis of (2R/S-trans)-3-(3-bromophenyl)-Oxiranemethanol (a) Trans-3-(3-bromophenyl)-2-propenoic acid A magnetically stirred solution of 3-bromobenzaldehyde (86.5 g, 0.468 mol) and malonic acid (107 g, 1.03 mol) in pyridine (200 ml) was treated with piperidine (4.0 ml, 40.45 mmol) and heated at ~90° C. for 90 min then under reflux for 30 min. The cooled mixture was poured onto ice (200 g) and water (300 ml) then acidified to pH=1 with conc. hydrochloric acid. Filtration afforded a white solid which was washed with water (4×200 ml), dried by suction and placed in an oven at 70° C. for 48 h until constant weight was obtained (96.02 g, 90%); $v_{max}$ (nujol)/cm$^{-1}$ 3400–2000 (br. OH), 1684.5, 1631.5, 1587.0; $\delta_H$ (270 MHz) 6.45 (1H, d, 2-H, $^3J_{2,3}$=16,2 Hz); 7.28 (1H, t, 5'-H, $J_o$=7.8 Hz); 7.48 (1-H, dt, 4'-H, $J_o$=7.9, $J_m$=1.3 Hz); 7.54 (1-H, dt, 6'-H, $J_o$=7.9, $J_m$=1.0 Hz); 7.70 (1-H, t, 2'-H, $J_m$=1.8 Hz); 7.71 (1H, d, 3-H, $^3J_{3,2}$=15.8 Hz).

(b) Methyl trans 3-(3-bromophenyl)-2-propenoate (first method)

A solution of trans-3-(3-bromophenyl)-2-propenoic acid (0.405 mol) in methanol (300 ml) was treated with conc. sulfuric acid (6.0 ml) and heated under reflux for 10 h. The cooled mixture was filtered to afford the title compound (46.14 g, 47%) as brilliant white crystals, m.p. 53°–55° C. (Found: C, 50.10; H, 3.58; Br; 33.21. $C_{10}H_9BrO_2$ requires C, 49.82; H, 3.76; Br, 33.14%); $v_{max}$ (nujol)/cm$^{-1}$ 1730.5, 1715.0, 1644; $\delta_H$ (270 MHz) 3.81 (3H, s, OC$\underline{H}_3$); 6.43 (1H, d, 2-H, $^3J_{2,3}$=16.2 Hz); 7.25 (1H, t, 5'-H, $J_o$=7.8 Hz); 7.43 (1H, dt, 4'-H, $J_o$=7.9, $J_m$=1.0 Hz); 7.50 (1H, dt, 6'-H, $J_o$=7.9, $J_m$=1.0 Hz); 7.60 (1H, d, 3-H, $^3J_{3,2}$=16.2 Hz); 7.66 (1H, t, 2'-H, $J_m$=1.7 Hz). $\delta_C$ (67.8 MHz) 51.8 (O$\underline{C}H_3$); 123.0 (3'-C); 133.0 (4'-C); 136.4 (1'-C); 143.1 (3-C); 166.9 ($\underline{C}O_2$Me). Remaining signals lie in the range 119.3–130.7 ppm; m/z 242.0, 240.0 (46.67, 47.64, M$^+$), 211.0, 209.0 (72.69, 74.00), 182.9, 180.9 (15.67, 16.83), 161.0 (4.19), 130.0 (9.44), 102.1 (100).

The filtrate was evaporated in vacuo to give a brown solid which was dissolved in ethyl acetate (400 ml), washed with 10% aqueous sodium bicarbonate (2×300 ml), dried ($Na_2SO_4$) and evaporation of the solvent provided the title product as off-white crystals (48.80 g, 50%).

(c) Ethyl trans-3-(3-bromophenyl)-2-propenoate

A magnetically stirred solution of triethyl phosphonoacetate (12.12 g, 54.0 mmol) in dry tetrahydrofuran (30.0 ml) at −10° C. under an $N_2$ atmosphere was treated portionwise with a 60% dispersion of sodium hydride in mineral oil (2.16 g, 54.0 mmol). Resulting solution was stirred below 10° C. for 1 h, cooled to −5° C. and treated with a solution of 3-bromobenzaldehyde (10.0 g, 54.0 mmol) in THF (20.0 ml) dropwise. The reaction mixture was stirred below 25° C. for 3 h, quenched with water (300 ml), extracted into ethyl acetate (3×100 ml), the combined organic extracts were washed with brine (2×100 ml), dried ($Na_2SO_4$) and the solvent was removed in vacuo to reveal a pale yellow oil. Dissolution in light petroleum (b.p. 30°–40° C.) (50.0 ml) and cooling to −30° C. afforded the title compound (11.94 g, 87%) as a white crystalline solid, m.p. 26°–28° C.; (Found C, 52.03; H, 4.20; Br, 31.38. $C_{11}H_{11}BrO_2$ requires C, 51.79; H, 4.35; Br, 31.32%); $v_{max}$ (thin film)/cm$^{-1}$ 3062.0, 2981.0, 1717.0, 1640.0, 1592; $\delta_H$ (270 MHz) 1.34 (3H, t, $CH_2$C$\underline{H}_3$, $^3J$=7.1 Hz); 4.27 (2H, q, C$\underline{H}_2$CH$_3$, $^3J$=7.3 Hz); 6.43 (1H, d, 2-H, $^3J_{2,3}$=15.8 Hz); 7.25 (1H, t, 5'-H, $J_o$=7.9 Hz); 7.43 (1H, dd, 4'-H, $J_o$=7.6, $J_m$=1.0 Hz); 7.50 (1H, dt, 6'-H, $J_o$=7.9, $J_m$=1.0 Hz); 7.60 (1H, d, 3-H, $^3J_{3,2}$=16.2 Hz); 7.66 (1H, t, 2'-H, $J_m$=1.8 Hz). $\delta_C$ (67.8 MHz) 14.3 (OCH$_2$$\underline{C}H_3$); 66.7 (O$\underline{C}H_2$CH$_3$); 123.0 (3'-C); 133.0 (4'-C); 136.6 (1'-C); 142.8 (3-C); 166.5 ($\underline{C}O_2$Me). Remaining signals lie in the range 119.7–130.7 ppm; m/z 256.9, 254.9 (2.46, 3.99, M$^+$), 255.9, 254.0 (21.6, 22.26), 227.9, 226.0 (9.49, 9.51), 210.9, 208.9 (46.92, 47.72), 184.9, 182.9 (95.49, 100), 156.9, 154.9 (51.38, 52.63), 102.0 (56.89).

(d) Methyl trans-3-(3-bromophenyl)-2-propenoate (second method)

Prepared in accordance with the above procedure using methyl diethyl phosphonoacetate to afford the title compound as white crystals (57%). Physical and spectroscopic data for this compound were as described above.

(e) Trans-3-(3-bromophenyl)-2-propenol

A vigorously stirred solution of ethyl trans-3-(3-bromophenyl)-2-propenoate (26.71 g, 0.105 mol) in dry toluene (150 ml) at −5° C. (ice-EtOH) under nitrogen was treated with lithium aluminium hydride (3.98 g, 0.105 mol) in one portion. The reaction temperature was allowed to gradually warm to room temperature over 30 min., at 25° C. the reaction became quite exothermic (25°–40° C.) with the formation of a grey gelatinous precipitate. Stirring was continued for 1 h, after which the reaction was carefully quenched with water (300 ml) and ice (200 g) then allowed to stand at 25° C. for 30 min. The mixture was filtered through Celite (Registered Trade Mark) and the residue was washed with ethyl acetate (2×200 ml). The filtrate was extracted with the organic washings, the combined organic phases were washed with brine (3×300 ml), water (300 ml), dried ($Na_2SO_4$) and evaporated to give the title compound as a pale yellow oil (21.42 g, 96%). Distillation at 120° C. at 0.05 mmHg. gave a colourless oil. (Found C, 50.73; H, 4.12; Br, 37.53. $C_9H_9BrO$ requires C, 50.73; H, 4.26; Br, 37.50%); $v_{max}$ (thin film)/cm$^{-1}$ 3325.5 (br. OH), 2862.0, 1653.0, 1591.0, 1562.5; $\delta_H$ (270 MHz) 2.15 (1H, bs, 1-OH), 4.30 (2H, dd, 2×1-H, $^3J_{1,2}$=5.5, $^4J_{1,3}$1.5 Hz), 6.33 (1H, dt, 2-H, $^3J_{2,3}$=15.8, $^3J_{2,1}$=5.3 Hz), 6.53 (1H, dt, 3-H, $^3J_{3,2}$=16.2, $^4J_{3,1}$=1.3 Hz), 7.15 (1H, t, 5'-H, $J_o$=7.8 Hz), 7.26 (1H, dt, 6'-H, $J_o$=7.6, $J_m$=1.3 Hz), 7.35 (1H, dt, 4'-H, $J_o$=7.9, $J_m$=1.6 Hz), 7.50 (1H, t, 2'-H, $J_m$=1.6 Hz). $\delta_C$ (67.8 MHz) 63.2 (1-C), 122.7 (3'-C), 125.0 (2-C), 129.2 (5'-H), 138.8 (1'-C). The remaining signals fall in the narrow range 130.0 to 130.4 ppm; m/z 214.1, 212.1 (44.86,49.78, M$^+$), 196.0, 194.0 (1.47, 1.03), 185.0, 183.0 (10.81, 12.19), 172.0, 170.0 (46.47, 49.07), 158.0, 156.0 (15.47, 15.80), 133.1, 131.1 (36.29, 25.66), 104.1 (100).

(f) (2S-Trans)-3-(3-bromophenyl)oxiranemethanol

A magnetically stirred solution of L-(+)-diethyl tartrate (2.69 g, 13.11 mmol) in dry dichloromethane (60.0 ml) at −30° C. under nitrogen was treated sequentially with powdered 4 Å molecular sieves (10.93 g), titanium(IV) isopropoxide (2.65 ml, 8.74 mmol) and a 3.0 M solution of tert-butyl hydroperoxide in isooctane (74.4 ml, 0.223 mol). The resulting white suspension was stirred below −10° C. for 2 h. then treated dropwise with a solution of trans-3-(3-bromophenyl)-2-propenol (23.24 g, 0.109 mol) in dichloromethane (30.0 ml) at −30° C. Stirred between −10° and −30° C. for 6 h treated with a solution of 10% NaOH in saturated brine (135 ml), stirring was continued below 10° C. for 30 min. after which a mixture of $MgSO_4$ (29.75 g, 0.248 mol) and celite (20.31 g) was added. After stirring at room temperature for 1 h. the mixture was filtered through Celite and the residue was washed with dichloromethane (3×100 ml). The combined organic filtrates were washed with brine (3×300 ml), dried ($Na_2SO_4$) and evaporated to give a yellow oil (27.78 g). Column chromatography (ethyl acetate—light petroleum (b.p. 40°–60° C.), 3:7) provided the title compound (17.24 g, 70%) as a pale yellow oil. Distilled at 160°–185° C. at 0.1 mmHg. using a Kugelrohr short path distillation apparatus as a colourless oil. (Found C, 47.36; H, 4.01; Br, 34.31. $C_9H_9BrO_2$ requires C, 47.19; H, 3.96; Br, 34.88%); $[\alpha]_D^{25}$ −38.9 (c=0.017 gml$^{-1}$, CHCl$_3$); $v_{max}$ (nujol)/cm$^{-1}$ 3401.5 (br. OH), 2926.5, 1598.5, 1571.0; $\delta_H$ (270 MHz) 2.20 (1H, bq, OH, $^3J_{OH,1-H}$=7.4, $^3J_{OH,1'-H}$=5.4 Hz); 3.18 (1H, m, 2-H); 3.80 (1H, dq, 1-H, $^2J_{1,1'}$=12.9, $^3J_{1,OH}$=7.4, $^3J_{1,2}$=3.8 Hz); 3.91 (1H, d, 3-H, $^3J_{3,2}$=2.3 Hz); 4.04 (1H, dq, 1'-H, $^2J_{1',1}$=12.9, $^3J_{1',OH}$=5.0, $^3J_{1',2}$=2.3 Hz); 7.22 (2H, m, 5'-H, 6'-H); 7.43 (2H, m, 2'-H, 4'-H). $\delta_C$ (67.8 MHz) 50.4 (2-C); 56.65 (1-C); 58.3 (3-C); 118.4 (3'-C); 120.1 (6'-C); 134.8 (1'-C). The remaining signals lie in the range 124.3–127.1 ppm; m/z 229.9, 227.9 (8.09, 8.87, M$^+$), 215.9, 213.9 (12.78, 14.91), 185.9, 183.9 (14.24, 182.9), 104.0 (44.32), 89.1 (100).

(g) (2R)-(+)-Trans-3-(3-bromophenyl)oxiranemethanol

The title compound was prepared from trans-3-(3-bromophenyl)-2-propenol by a sequence analogous to that described above for compound (9a) but using D-(−)-diethyl tartrate. Column chromatography (ethyl acetate—light petroleum (b.p. 40°–60° C.), 3:7) provided the title compound (73%) as a pale yellow oil. Distilled at 160°–185° C. at 0.1 mmHg. using a Kugelrohr short path distillation apparatus as a colourless oil; $[\alpha]_D^{25}$ +37.6 (c=0.020 gml$^{-1}$, CHCl$_3$).

(h) Preparation of racemic trans-3-(3-bromophenyl) oxiranemethanol

A magnetically stirred solution of m-chloroperbenzoic acid (3.57 g, 10.33 mmol) in dichloromethane (60.0 ml) at 25° C. was treated dropwise with a solution of trans-3-(3-bromophenyl)-2-propenol (2.0 g, 9.39 mmol) in dichloromethane (20.0 ml). After stirring for 16 h the mixture was diluted with dichloromethane (200 ml), washed with aqueous 1M NaOH (2×200 ml), brine (2×200 ml) and dried ($Na_2SO_4$). Evaporation of the solvent in vacuo returned the crude epoxide as a pale yellow oil (2.06 g). Column chromatography (ethyl acetate—light petroleum (b.p. 40°–60° C.), 3:7) provided the title compound (1.53 g, 71%) as a pale yellow oil.

EXAMPLE 1

Synthesis of (2S,3R)-(−)-3-(3-bromophenyl)-3-(7-benzyloxyindolin-1-yl)propane-1,2-diol Magnesium perchlorate (16.63 g, 74.52 mmol) was added in portions to a magnetically stirred solution of (2S-trans)-3-(3-bromophenyl)oxiranemethanol (16.32 g, 71.26 mmol) in dry acetonitrile (100 ml) at 5° C. under nitrogen. After stirring for 10 min. all of the magnesium salts had dissolved and the resulting intense yellow solution was treated with 7-benzyloxyindoline (16.77 g, 74.52 mmol) in acetonitrile (30.0 ml) dropwise at 0° C. (ice-H$_2$O). The dark brown solution was stirred at 25° C. for 20 h, quenched with saturated aqueous NaHCO$_3$ (300 ml), extracted with ethyl acetate (3×200 ml), the combined organic phases were washed with brine (3×200 ml), dried (Na$_2$SO$_4$) and the solvent removed in vacuo to provide a yellow/brown gum. Column chromatography (ethyl acetate—light petroleum (b.p. 40°–60° C.), 3:7) provided the title compound (27.37 g, 87%) as a grey/green oil which crystallised on standing. Recrystallised from diethyl ether at −20° C. as white crystals, m.p. 61°–66° C. (Found: C, 63.51; H, 5.78; N, 2.84. C$_{24}$H$_{24}$BrNO$_3$ requires C, 63.44; H, 5.32; N, 3.08%); $[\alpha]_D^{25}$ −311.1 (c=0.009 gml$^{-1}$, CHCl$_3$); $v_{max}$ (nujol)/cm$^{-1}$ 3353.0 (br. OH), 1584.0, 1565.0; $\delta_H$ (270 MHz) 2.27 (1H, bs, OH); 2.66 (3H, m, OH, 2×indoline 2-H); 3.10 (1H, m, indoline 3-H); 3.30 (1H, m, indoline 3-H); 3.85 (2H, dq, 2×1-H, $^2J_{1,1}$=11.5, $^3J_{1,2}$=4.0 Hz); 4.22 (1H, m, 2-H); 5.16 (2H, s, C H$_2$Ph); 5.38 (1H, d, 3-H, $^3J_{3,2}$=10.2 Hz); 6.65–7.49 (12H, m, 12 ArH). $\delta_C$ (67.8 MHz) 29.2 (indoline 2-C); 46.5 (indoline 3-C); 61.7 (3-C); 64.8 (1-C); 69.9 (C-2); 70.9 (CH$_2$Ph); 112.2 (indoline 6-C); 118.1 (indoline 5-C); 120.3 (indoline 4-C); 122.4 (3'-C); 136.4 (1'-C); 138.5 (indoline 7a-C);

139.5 (benzyl ipso-C); 145.0 (indoline 7-C). The remaining signals lie between 127.5–136.4 ppm and could not be assigned with any certainty; m/z 455.3, 453.3 (0.58, 0.74, M+), 394.2, 392.2 (7.81, 7.90), 304.1, 302.1 (4.80, 9.32), 225.2 (8.35), 171.0, 169.0 (5.29, 5.79), 134.1 (34.82), 118.1 (1.35), 59.1 (100).

EXAMPLE 2

Synthesis of (2R,3S)-(+)-3-(3-bromophenyl)-3-(7-benzyloxyindolin-1-yl)propane-1,2-diol The title compound was prepared from (2R-trans)-3-(3-bromophenyl)oxiranemethanol by a sequence analogous to that described above in Example 1. Column chromatography (ethyl acetate—light petroleum (b.p. 40°–60° C.), 3:7) provided the title compound (77%) as a grey/brown foam. Recrystallised from diethyl ether at −20° C. as brown/grey prisms, m.p. 59°–60° C.; $[\alpha]_D^{25}$ +312.9 (c=0.009 gml$^{-1}$, CHCl$_3$).

EXAMPLE 3

Synthesis of (1R/S)-(+/−)-7-chloro-2-(2-{3-[1-(7-{1H-tetrazol-5-ylmethoxy}indol-1-yl)-4-(1H-tetrazol-5-yl)butyl]phenyl}ethenyl)quinoline (a) (2S,3R)-(−)-7-Benzyloxy-1-[1-(3-bromophenyl)-1-(1,3-dioxolane-2-thione-4-yl)methyl]indoline A solution of (2S,3R)-(−)-3-(3-bromophenyl)-3-(7-benzyloxyindolin-1-yl)propane-1,2-diol (11.42 g, 25.72 mmol), 1,1'-thiocarbonyldiimidazole (6.50 g, 36.47 mmol) and 4-dimethylaminopyridine (0.10 g, 0.82 mmol) in dry dichloromethane (120 ml) was stirred at 25° C. under nitrogen for 4 h and adsorbed onto silica (ca. 25.0 g). Column chromatography (ethyl acetate—light petroleum (b.p. 40°–60° C.), 1:4) provided the title compound (11.66 g, 91%) as a pale yellow oil which crystallised on standing to afford an orange/brown foam. (Found: C, 60.82; H, 4.31; N, 2.61; Br, 16.21; S, 6.28. C$_{25}$H$_{22}$BrNO$_3$S requires C, 60.49; H, 4.47; N, 2.82; Br, 16.10; S, 6.46%); $[\alpha]_D^{25}$ −198° (c=0.007 gml$^{-1}$, CHCl$_3$); ν$_{max}$ (nujol)/cm$^{-1}$ 1591; δ$_H$ (270 MHz) 2.70 (2H, m, 2×indoline 2-H); 3.05 (1H, m, indoline 3-H); 3.25 (1H, m, indoline 3-H); 4.76 (2H, m, dioxolane 2×4-H); 5.17 (2H, q, C$\underline{H}_2$Ph, $^2J$ =11.1 Hz); 5.37 (1H, m, dioxolane 5-H); 5.72 (1H, d, 1-H, $^3J_1$,dioxolane 4-H=10.2 Hz); 6.80 (3H, m, indoline 4-H, 5-H, 6-H); 7.06–7.48 (10H, m, 10ArH). δ$_C$ (67.8 MHz) 29.2 (2-C); 47.0 (3-C); 61.5 (1'-C); 70.89 (C$\underline{H}_2$Ph); 73.0 (dioxolane 5-C); 79.6 (dioxolane 4-C); 111.9 (6-C); 118.0 (5-C); 121.2 (4-C); 122.7 (3'-C); 136.0 (benzyl ipso-C); 145.4 (7-C); 191.5 (dioxolane 2-C). The remaining signals lie between 126.8–131.1 ppm; m/z 497.2, 495.2 (3.60, 3.82, M+), 394.3, 392.3 (8.34, 8.38), 330.2, 328.1 (6.08, 7.09), 225.1 (14.70), 134.0 (75.04), 118.1 (5.81), 91.1 (100).

(b) (2R,3S)-(+)-7-Benzyloxy-1-[1-(3-bromophenyl)-1-(1,3-dioxolane-2-thione-4-yl)methyl]indoline The title compound was prepared from (2R,3S)-(+)-3-(3-bromophenyl)-3-(7-benzyloxyindolin-1-yl)propane-1,2-diol by a sequence analogous to that described immediately above. Column chromatography (ethyl acetate—light petroleum (b.p. 40°–60° C.), 1:4) provided the title compound (87%) as a yellow foam; $[\alpha]_D^{17}$ +217 (c=0.011 gml$^{-1}$, CHCl$_3$).

(c) (1R)-(−)-7-Benzyloxy-1-[1-(3-bromophenyl)prop-2-enyl]indoline

A magnetically stirred solution of (2S,3R)-(−)-7-benzyloxy-1-[1-(3-bromophenyl)-1-(1,3-dioxolane-2-thione- 4-yl)methyl]indoline (11.60 g, 23.39 mmol) in dry tetrahydrofuran (80.0 ml) under nitrogen was treated with 1,3-dimethyl-2-phenyl-1,3,2-diazaphospholidine (10.8 ml, 58.47 mmol) in one portion. The mixture was degassed and flushed with nitrogen (×3) then heated at 50°–60° C. for 7 h. The cooled solution was adsorbed onto silica (ca. 30.0 g) and column chromatography (ethyl acetate—light petroleum (b.p. 40°–60° C.), 1:9) gave the title compound as a golden yellow oil (8.50 g, 87%). (Found C, 68.65; H, 5.10; N, 3.25; Br, 18.90. C$_{24}$H$_{22}$BrNO requires C, 68.58; H, 5.28; N, 3.33; Br, 19.01%); $[\alpha]_D^{25}$ −93° (c=0.012 gml$^{-1}$, CHCl$_3$); ν$_{max}$ (thin film)/cm$^{-1}$ 3063.5, 3031.5, 2939.0, 1591.0, 1566.5, 1483.5; δ$_H$ (270 MHz) 2.90 (2H, m, 2×indoline 2-H); 3.23 (1H, m, indoline 3-H); 3.39 (1H, m, indoline 3-H); 5.04 (2H, q, C$\underline{H}_2$Ph, $^2J$=11.6 Hz); 5.08–5.34 (2H, m, 2×3-H); 6.11 (2H, m, 1-H, 2-H); 6.70 (3H, m, indoline 4-H, 5-H, 6-H); 7.14 (1H, t, 5'-H, J$_o$=7.9 Hz); 7.22–7.39 (7H, ArH); 7.50 (1H, t, 2'-H, J$_m$=1.5 Hz). δ$_C$ (67.8 MHz) 29.2 (2-C); 47.5 (3-C); 62.2 (1'-C); 70.9 (C$\underline{H}_2$Ph); 112.9 (6-C); 118.1 (5-C); 118.9 (3-C*); 119.5 (4-C*); 122.4 (3'-C); 135.0 (benzyl ipso-C); 143.6 (7a-C); 145.1 (7-C). The remaining signals lie between 126.6–129.8 ppm and could not be assigned with any certainty; m/z 421.3, 419.3 (11.95, 13.72), 330.2, 328.1 (34.60, 37.43), 224.2 (20.33), 197.0, 195.0 (13.59, 14.40), 134.1 (37.57), 116.1 (100).

* These signals may be interchangeable.

(d) (1S)-(+)-7-Benzyloxy-1-[1-(3-bromophenyl)prop-2-enyl]indoline

The title compound was prepared from (3S,2R)-(+)-7-benzyloxy-1-[1-(3-bromophenyl)-1-(1,3-dioxolane-2-thione-4-yl)methyl]indoline by a sequence analogous to that described immediately above. Column chromatography (ethyl acetate—light petroleum (b.p. 40°–60° C.), 1:9) provided the title compound (83%) as a pale yellow oil; $[\alpha]_D^{17}$ +97 (c=0.010 gml$^{-1}$, CHCl$_3$).

(e) (3R)-(−)-3-(3-Bromophenyl)-3-(7-benzyloxyindolin-1-yl)propan-1-ol

A 1.0M solution of borane-tetrahydrofuran complex (BH$_3$—THF) in tetrahydrofuran (38.1 ml, 38.10 mmol) was added dropwise to a magnetically stirred solution of (1R)-(−)-7-benzyloxy-1-[1-(3-bromophenyl)prop-2-enyl]indoline (16.0 g, 38.1 mmol) in dry tetrahydrofuran (200 ml) under nitrogen at 0° C. The reaction mixture was heated under reflux for 8.5 h, during which time two further aliquots of 1.0M BH$_3$—THF in tetrahydrofuran were added (1×15.0 ml and 1×5.0 ml) until TLC inspection indicated that no further starting olefin remained. The reaction mixture was cooled to 0° C., sequentially treated with water (21.0 ml), 3M sodium hydroxide solution (21 ml) and 30% hydrogen peroxide (21.0 ml) then stirred at room temperature for 16 h. Quenched with brine (400 ml), extracted with ethyl acetate (3×200 ml), the combined organic phases were washed with brine (200 ml), dried (Na$_2$SO$_4$) and evaporated to yield a brown oil. Column chromatography (ethyl acetate—light petroleum (b.p. 40°–60° C.), 1:4) gave the title compound as a pink oil (11.70 g, 70%). $[\alpha]_D^{25}$ −280° (c=0.011 gml$^{-1}$, CHCl$_3$); ν$_{max}$ (thin film)/cm$^{-1}$ 3391 (br. OH), 3063, 3031, 2939, 1591; δ$_H$ (270 MHz) 1.89 (1H, m, 1×2-H); 2.26 (1H, m, 1×2-H); 2.69 (2H, m, indoline 2×2-H); 3.13 (1H, m, indoline 1×3-H); 3.30 (1H, bs, 1-OH); 3.43 (1H, m, indoline 1×3-H); 3.81 (2H, m, 2×1-H); 5.17 (2H, s, C$\underline{H}_2$Ph); 5.59 (1H, dd, 3-H, $^3J_{3,2}$=11.2 Hz, $^3J_{3,2'}$=4.0 Hz); 6.77 (3H, m, indoline 4-H, 5-H, 6-H); 7.06 (2H, m, 5'-H, 6'-H); 7.31–7.51 (7H, ArH). δ$_C$ (67.8 MHz) 29.1 (2-C); 32.7 (indoline 2-C); 45.6 (indoline 3-C); 58.2 (1-C); 61.7 (3-C); 70.9 (C$\underline{H}_2$Ph); 112.2 (indoline 6-C); 118.1 (indoline 5-C); 120.6 (indoline 4-C); 122.3 (3'-C); 133.4 (indoline 3a-C); 136.7 (1'-C); 139.0 (benzyl ipso-C); 142.4 (indoline 7a-C); 145.7 (indoline 7-C). The remaining signals lie between 126.5–130.7 ppm and cannot be assigned with any certainty; m/z 439.1, 437.1 (2.69, 3.32, M+), 394.2, 392.2 (1.06, 1.09), 348.1, 346.1 (5.33, 5.60), 225.1 (18.26), 172.0, 170.0 (33.75, 34.31), 134.0 (100), 118.0 (2.79), 91.1 (67.26).

(f) (3S)-(+)-3-(3-Bromophenyl)-3-(7-benzyloxyindolin-1-yl)propan-1-ol

The title compound was prepared from (1S)-(+)-7-benzyloxy-1-[1-(3-bromophenyl)]prop-2-enylindoline by a sequence analogous to that described immediately above. Column chromatography (ethyl acetate—light petroleum (b.p. 40°–60° C.), 1:4) provided the title compound (70%) as a pink oil; $[\alpha]_D^{17}$ +280 (c=0.010 gml$^{-1}$, CHCl$_3$).

(g) (3R)-(−)-3-(3-Bromophenyl)-3-(7-benzyloxyindol-1-yl)propan-1-ol

A stirred solution of (3R)-(−)-3-(3-bromophenyl)-3-(7-benzyloxyindolin-1-yl)propan-1-ol (1.0 g, 2.28 mmol) in dry dichloromethane (30.0 ml) under nitrogen at 5° C. was treated with triethylamine (0.52 ml, 3.77 mmol) followed by chlorotrimethylsilane (0.32 ml, 2.52 mmol) dropwise. The resulting suspension was stirred at room temperature for 20 min, treated with 2,3-dichloro-5, 6-dicyano-1,4-benzoquinone (0.57 g, 2.52 mmol) and stirred at room temperature until the reaction was judged to be complete from TLC inspection (~30 min). The solvent was removed by evaporation, the residue was taken up in ethyl acetate (200 ml), washed with 2M aqueous sodium hydroxide (3×100 ml), brine (100 ml) and 2M aqueous hydrochloric acid (2×100 ml). Evaporation of the dried organic extracts (Na$_2$SO$_4$) gave a yellow/brown oil. Column chromatography (ethyl acetate—light petroleum (b.p. 40°–60° C.), 1:4) gave the title compound as a yellow oil (0.80 g, 80%). $[\alpha]_D^{26}$ −157 (c=0.014 gml$^{-1}$, CHCl$_3$); $\nu_{max}$ (thin film)/cm$^{-1}$ 3418.5 (br. OH), 3064.5, 3033.5, 2935.5, 2879.0, 1593.5, 1570.5; $\delta_H$ (270 MHz) 2.35 (2H, m, 2×2-H); 3.50 (2H, m, 2×1-H); 5.13 (2H, q, CH$_2$Ph, $^2$J=11.1 Hz); 6.6 (m, 2H, 3-H, indole 3-H); 6.72 (1H, dd, indole 6-H, J$_o$=7.6 Hz, J$_m$=0.7 Hz); 6.90 (1H, dd, indole 4-H, J$_o$=8.3 Hz, J$_m$=0.8 Hz); 7.00 (2H, m, indole 5-H, 5'-H); 7.15 (1H, d, indole 2-H, $^3$J$_{2,3}$=3.0 Hz); 7.19–7.40 (8H, m, 8ArH). $\delta_C$ (67.8 MHz) 38.4 (2-C); 56.4 (3-C); 59.3 (1-C); 70.7 (PhCH$_2$); 103.2 (indole 3-C); 104.3 (indole 6-C); 114.3 (indole 4-C); 120.1 (indole 5-C); 122.5 (3'-C); 125.0 (indole 2-C); 131.8 (1'-C); 136.4 (benzyl ipso-C); 144.9 (indole 7a-C); 146.5(indole 7-C). The remaining signals lie between 126.5–130.7 ppm and cannot be assigned with any certainty.

(h) (3S)-(+)-3-(3-Bromophenyl)-3-(7-benzyloxyindol-1-yl)propan-1-ol

The title compound was prepared from (3S)-(+)-3-(3-bromophenyl)-3-(7-benzyloxyindolin-1-yl) propan-1-ol (13b) by a sequence analogous to that described immediately above. Column chromatography (ethyl acetate—light petroleum (b.p. 40°–60° C.), 1:4) provided the title compound (74%) as a yellow/brown oil; $[\alpha]_D^{22}$ +188 (c=0.007 gml$^{-1}$, CHCl$_3$).

(i) (1R)-(−)-7-Benzyloxy-1-[1-(3-bromophenyl)-4-cyanobutyl]indole

Acetonitrile (2.72 ml, 52.19 mmol) in dry tetrahydrofuran (5.0 ml) was added dropwise to a magnetically stirred solution of 2.5M n-butyllithium in hexane (22.0 ml, 54.80 mmol) in tetrahydrofuran (100 ml) at −75° C. under nitrogen. The resulting white suspension was stirred below −70° C. for 1 h to ensure complete formation of the lithio acetonitrile reagent.

A solution of (3R)-(−)-3-(3-bromophenyl)-3-(7-benzyloxyindol-1-yl) propan-1-ol (5.10 g, 11.62 mmol) and 2,6-lutidine (1.24 g, 11.62 mmol) in dry dichloromethane (20.0 ml) was added dropwise to a magnetically stirred solution of trifluoromethanesulfonic anhydride (2.20 ml, 13.10 mmol) in dichloromethane (40.0 ml) at −10° C. under nitrogen over a 25 min. period. The resulting grey solution was stirred below −10° C. for 20 min., quenched with water (250 ml), extracted into dichloromethane (2×200 ml), the combined organic extracts were washed with water (200 ml), dried (Na$_2$SO$_4$) and the solvent removed in vacuo at room temperature to give an orange/brown oil which was dissolved in dry tetrahydrofuran (40.0 ml) and added dropwise to the stirred lithio acetonitrile reagent(52.19 mmol) in tetrahydrofuran at −70° C. TLC inspection immediately after the addition showed that the reaction was complete. Quenched with water (20.0 ml), diluted with ethyl acetate (300 ml), washed with brine (2×200 ml), dried (Na$_2$SO$_4$) and adsorbed onto silica (ca. 12.0 g). Column chromatography (ethyl acetate—light petroleum (b.p. 40°–60° C.), 1:4) gave the title compound as a pale yellow oil (4.17 g, 78%). (Found: C, 67.62; H, 5.04; N, 5.94; Br, 17.60. C$_{26}$H$_{23}$BrN$_2$O requires C, 67.98; H, 5.05; N, 6.10; Br, 17.39%); $[\alpha]_D^{19}$ −138 (c=0.010 gml$^{-1}$, CHCl$_3$); $\nu_{max}$ (thin film)/cm$^{-1}$ 3064, 2934, 2871, 2246.5 (CN), 1575; $\delta_H$ (270 MHz) 1.55 (2H, m, 2×butyl 3-H); 2.23 (2H, t, 2×butyl 4-H, $^3$J$_{4,3}$=6.9 Hz); 2.30 (2H, m, 2×butyl 2-H); 5.17 (2H, q, CH$_2$Ph, $^2$J×10.9 Hz); 6.35 (1H, dd, butyl 1-H, $^3$J$_{1,2}$=9.7, $^3$J$_{1,2'}$=5.8 Hz); 6.56 (1H, d, 3-H, $^3$J$_{3,2}$=3.3 Hz); 6.74 (1H, d, 6-H, J$_o$=7.9 Hz); 6.95 (1H, d, 4-H, J$_o$=7.9 Hz); 7.00 (1H, t, 5-H, J$_o$=7.9 Hz); 7.08 (1H, t, 5'-H, J$_o$=7.9 Hz); 7.14 (1H, d, 2-H, $^3$J$_{3,2}$=3.3 Hz); 7.21 (1H, d, 6'-H, J$_o$=8.9 Hz); 7.25 (1H, t, 2'-H, J$_m$=1.1 Hz); 7.34 (1H, dd, 4'-H, J$_o$=8.4, J$_m$=1.5 Hz); 7.42 (5H, m, 5ArH). $\delta_C$ (67.8 MHz) 16.5 (butyl 3-C); 22.3 (butyl 4-C); 34.4 (butyl 2-C); 58.8 (butyl 1-C); 70.6 (PhCH$_2$); 103.5 (indole 3-C); 104.1 (indole 6-C); 114.2 (indole 4-C); 119.1 (CN); 120.2 (indole 5-C); 122.6 (3'-C); 124.5 (indole 2-C); 125.0 (6'-C); 130.7 (1'-C); 136.5 (benzyl ipso-C); 144.2 (indole 7a-C); 147.0 (indole 7-C). The remaining signals lie between 128.2–130.6 ppm and cannot be assigned with any certainty; m/z 460.1, 458.1 (3.43, 3.32), 369.1, 367.1 (1.79, 1.66), 239.0, 237.0 (7.01, 7.72), 171.0, 169.0 (26.03, 26.07), 143.1 (100), 132.1 (6.44), 116.0 (9.37).

(j) (1S)-(+)-7-Benzyloxy-1-[1-(3-bromophenyl)-4-cyanobutyl]indole

The title compound was prepared from (3S)-(+)-3-(3-bromophenyl)-3-(7-benzyloxyindol-1-yl) propan-1-ol by a sequence analogous to that described above for the R-enantiomer. Column chromatography (ethyl acetate—light petroleum (b.p. 40°–60° C.), 1:4) provided the title compound (51%) as a yellow oil; $[\alpha]_D^{20}$ +153 (c=0.011 gml$^{-1}$, CHCl$_3$).

(k) (1R)-(−)-1-[1-(3-Bromophenyl)-4-cyanobutyl]-7-cyanomethoxyindole

The title compound was prepared from (1R)-(−)-7-benzyloxy-1-[1-(3-bromophenyl)-4-cyanobutyl]indole (4.34 g, 9.45 mmol) by a sequence analogous to that described below for step (c) Example 4. Standard workup and column chromatography (ethyl acetate—light petroleum (b.p. 40°–60° C.), 1:4) gave the title compound as a pale yellow oil (2.70 g, 70%). (Found: C, 61.60; H. 4.34; N, 10.29. C$_{21}$H$_{18}$BrN$_3$O requires C, 61.78; H. 4.44; N, 10.29%); $[\alpha]_D^{25}$ −127 (c=0.008 gml$^{-1}$, CHCl$_3$) $\nu_{max}$ (thin film)/cm$^{-1}$ 3066.0, 2934.0, 2871.0, 2247.0 (CN), 1594, 1572.0; $\delta_H$ (270 MHz) 1.66 (2H, m, 2×butyl 3-H); 2.34 (2H, t, 2×butyl 4-H, $^3$J$_{4,3}$=6.9 Hz); 2.35 (2H, m, 2×butyl 2-H); 4.78 (2H, s, OCH$_2$CN); 6.18 (1H, dd, 1-H, $^3$J$_{1,2}$=8.9, $^3$J$_{1,2'}$=6.6 Hz); 6.59 (1H, 3-H, $^3$J$_{3,2}$=3.3 Hz); 6.65 (1H, d, 6-H, J$_o$=7.6 Hz); 7.01 (1H, t, 5-H, J$_o$=7.7 Hz); 7.12 (2H, m, 4-H, 6'-H); 7.20 (1H, d, 2-H, $^3$J$_{3,2}$=3.3 Hz); 7.30 (3H, m, 2'-H, 4'-H, 5'-H). $\delta_C$ (67.8 MHz) 16.8 (butyl 3-C); 22.4 (butyl 4-C); 34.5 (butyl 2-C); 53.6 (O$\underline{C}$H$_2$CN); 59.7 (butyl 1-C); 103.7 (indole 3-C); 104.4 (indole 6-C); 114.9 (OCH$_2$CN); 116.3 (indole 4-C); 119.1 (butyl CN); 120.0 (indole 5-C); 122.8 (3'-C); 125.0 (indole 2-C); 125.3 (6'-C); 125.7 (indole 3a-C); 129.3 (5'-C); 130.4 (4'-C); 130.8 (2'-C); 131.5 (1'-C); 143.9 (indole 7a-C); 144.0 (7-C).

(1) (1S)-(+)-1-[1-(3-Bromophenyl)-4-cyanobutyl]-7-cyanomethoxyindole

The title compound was prepared from (1S)-(+)-7-benzyloxy-1-[1-(3-bromophenyl)-4-cyanobutyl]indole by a sequence analogous to that described above for the R-enantiomer. Column chromatography (ethyl acetate—light petroleum (b.p. 40°–60° C.), 1:4) provided the title compound (39%) as a yellow oil; $[\alpha]_D^{20}$ +135 (c=0.009 gml$^{-1}$, CHCl$_3$).

(m) (1R)-(−)-7-Chloro-2-(2-{3-[1-(7-cyanomethoxyindol-1-yl)-4-cyanobutyl]phenyl}ethenyl)quinoline The title compound was prepared from (1R)-(−)-1-[1-(3-bromophenyl)-4-cyanobutyl]-7-cyanomethoxyindole by a sequence analogous to that described below in step (d) of Example 4. Column chromatography (ethyl acetate—light petroleum (b.p. 40°–60° C.), 1:4) provided the title compound (63%) as a grey/green oil. $[\alpha]_D^{19}$ −159 (c=0.00484 gml$^{-1}$, CHCl$_3$); $\nu_{max}$ (thin film)/cm$^{-1}$ 2245.5, 1607.5, 1575.5; $\delta_H$ (270 MHz) 1.67 (2H, m, 2×3-H); 2.42 (2H, t, 2×4-H, $^3J_{4,3}$=6.9 Hz); 2.42 (2H, m, 2×2-H); 4.83 (2H, s, OC$\underline{H}_2$CN); 6.28 (1H, dd, indole 1-H, $^3J_{1,2}$=8.9, $^3J_{1,2'}$=6.6 Hz); 6.61 (1H, d, indole 3-H, $^3J_{3,2}$=3.3 Hz); 6.69 (1H, d, indole 6-H, J$_o$=7.9 Hz); 7.04 (1H, t, 5'-H, J$_o$=7.9 Hz); 7.17 (1H, d, indole 4-H, J$_o$=7.9 Hz); 7.25–7.73 (10H, m, 10ArH); 8.09 (2H, m, 4-H, 8-H). $\delta_C$ (67.8 MHz) 16.9 (butyl 3-C); 22.5 (butyl 4-C); 53.8 (O$\underline{C}$H$_2$CN); 60.2 (butyl 1-C); 103.5 (indole 3-C); 104.4 (indole 6-C); 115.1 (OCH$_2$$\underline{C}$N); 116.4 (indole 4-C); 119.2 (CN); 119.7 (quinoline 3-C); 119.9 (indole 5-C); 135.2 (3'-C); 135.5 (quinoline 7-C); 136.2 (quinoline 4-C); 136.8 (1'-C); 142.1 (indole 7a-C); 144.1 (indole 7-C); 148.5 (quinoline 8a-C); 156.6 (quinoline 2-C). The remaining signals lie between 125.5 to 134.5 ppm.

(n) Trans-(1S)-(+)-7-Chloro-2-(2-{3-[-(7-cyanomethoxyindol-1-yl)-4-cyanobutyl]phenyl}ethenylquinoline The title compound was prepared from (1S)-(+)-1-[1-(3-bromophenyl)-4-cyanobutyl]-7-cyanomethoxy indole (19b) by a sequence analogous to that described above for the R-enantiomer. Column chromatography (ethyl acetate—light petroleum (b.p. 40°–60° C.), 1:4) provided the title compound (65%) as a yellow oil; $[\alpha]_D^{25}$ +157 (c=0.007 gml$^{-1}$, CHCl$_3$).

(o) (1R)-(−)-7-Chloro-2-(2-{3-[1-(7-{1H-tetrazol-5-ylimethoxy}indol-1-yl)-4-(1H-tetrazol-5-yl) butyl] phenyl}ethenyl)quinoline The title compound was prepared from (1R)-(−)-7-chloro-2-(2-{3-[1-(7-cyanomethoxyindol-1-yl)-4-cyanobutyl]phenyl}ethenyl)quinoline by a sequence analogous to that described below in step (e) of Example 4. Filtration gave the crude title compound as a mustard yellow solid (>100%). HPLC separation showed that this material was ~63% pure, which translates to a 70% yield for the reaction. $[\alpha]_D^{19}$ −126 (c=0.89 mgml$^{-1}$, CHCl$_3$); $\nu_{max}$ (thin film)/cm$^{-1}$ 3406 (br. NH), 1635.5, 1608.5, 1573.0; $\delta_H$ (270 MHz) 1.80 (2H, quintet, 2×butyl 2-H, $^3J$=7.8 Hz); 2.11 (1H, m, butyl 3-H); 2.29 (1H, m, butyl 3-H); 2.90 (2H, t, 2×butyl 1-H, $^3J_{1,2}$=7.3 Hz); 5.47 (2H, s, OC$\underline{H}_2$Tet); 6.40 (1H, t, butyl 4-H, $^3J_{4,3}$=8.1 Hz); 6.49 (1H, d, indole 3-H, $^3J_{3,2}$=3.3 Hz); 6.83 (1H, d, indole 6-H, J$_o$=7.3 Hz); 6.92 (2H, m, 2×ArH); 7.16 (4H, m, 4×ArH); 7.44 (4H, m, 4×ArH); 7.76 (1H, d, ArH, J$_o$=8.4 Hz); 7.87 (1H, d, quinoline 3-H, J$_o$=8.9 Hz); 7.90 (1H, d, quinoline 8-H, J$_m$=2.0 Hz); 8.17 (1H, d, quinoline 4-H, J$_o$=8.9 Hz).

(p) (1S)-(+)-7-Chloro-2-(2-{3-[1-(7-{1H-tetrazol-5-ylmethoxy}indol-1-yl)-4-(1H-tetrazol-5-yl) butyl] phenyl}ethenyl)quinoline The title compound was prepared from (1S)-(+)-7-chloro-2-(2-{3-[1-(7-cyanomethoxyindol-1-yl)-4-cyano butyl] phenyl}ethenyl)quinoline (21b) by a sequence analogous to that described above for the R-enantiomer. Filtration gave the crude title compound as a mustard yellow solid.

EXAMPLE 4

Synthesis of trans-(1R)-(−)-7-chloro-2-(2-{3-[1-(7-{1H-tetrazol-5-ylmethoxy}indol-1-yl)-3-(1H-tetrazol-5-yl) propyl]phenyl}ethenyl)quinoline.

(a) (3R)-3-(3-Bromophenyl)-3-(7-benzyloxyindol-1-yl) propan-1-yl methanesulfonate Methanesulfonyl chloride (0.20 ml, 2.61 mmol) in dry dichloromethane (4.0 ml) was added dropwise to a stirred solution of (3R)-(−)(3-bromophenyl)-3-(7-benzyloxyindolin-1-yl) propan-1-ol (1.04 g, 2.37 nmol prepared as in step (h) of Example 3) and triethylamine (0.73 ml, 5.20 mmol) in dichloromethane (30.0 ml) at −10° C. (ice-MeOH). The mixture was stirred below 10° C. for 20 min, treated with 2,3-dichloro-5,6-dicyano-1,4-benzoquinone (0.57 g, 2.44 mmol) in one portion then heated under reflux for 2.5 h. The cooled reaction mixture was adsorbed onto silica (ca. 5.0 g) and column chromatography (ethyl acetate—light petroleum (b.p. 40°–60° C.), 1:4) gave the title compound as a pale green oil (0.99 g, 81%). $\nu_{max}$ (thin film)/cm$^{-1}$ 3032.5, 2934.0, 1576.5, 1523.0; $\delta_H$ (270 MHz) 2.55 (2H, m, 2×propyl 2-H); 2.60 (3H, s, SO$_2$C$\underline{H}_3$); 3.98 (1H, m, 1×propyl 3-H); 4.14 (1H, m, 1×propyl 3-H); 5.11 (2H, q, C$\underline{H}_2$Ph, $^2J$=11.1 Hz); 6.56 (1H, m, propyl 1-H); 6.59 (1H, d, 3-H, $^3J_{3,2}$=3.3 Hz); 6.73 (1H, dd, 6-H, J$_o$=7.6, J$_m$=0.7 Hz); 6.88 (1H, dd, 4-H, J$_o$=7.6, J$_m$=0.9 Hz); 7.00 (1H, t, 5-H, J$_o$=7.9 Hz); 7.06 (1H, t, 5'-H, J$_o$=7.9 Hz); 7.21 (1H, d, 2-H, $^3J_{2,3}$=3.3 Hz); 7.24 (1H, dd, 6'-H, J$_o$=7.9, J$_m$=1.0 Hz); 7.38 (7H, m, 7 ArH). $\delta_C$ (67.8 MHz) 35.2 (propyl 2-C); 36.6 (SO$_2$$\underline{C}$H$_3$); 56.2 (propyl 3-C); 70.5 (Ph$\underline{C}$H$_2$); 103.8 (indole 3-C); 104.3 (indole 6-C); 114.2 (indole 4-C); 120.4 (indole 5-C); 122.6 (3'-C); 124.6 (indole 2-C); 130.8 (1'-C); 136.5 (benzyl ipso-C); 143.9 (indole 7a-C); 146.6(indole 7-C). The remaining signals lie between 128.1–130.6 ppm and cannot be assigned with any certainty; m/z 514.8, 512.9 (3.05, 3.03, M$^+$), 328.9, 326.8 (1.64, 1.79), 293.8, 291.8 (2.83, 2.74), 197.8, 195.8 (99.25, 100), 170.8, 168.8 (63.59, 67.93), 132.0 (8.98), 116.0 (27.78).

(b) (1R)-(−)-7-Benzyloxy-1-[1-(3-bromophenyl)-3-cyanopropyl]indole

A solution of (3R)-3-(3-bromophenyl)-3-(7-benzyloxyindol-1-yl) propan-1-yl methanesulfonate (2.50 g, 4.86 mmol prepared as in Example 3, step (i) ) and tetrabutylammonium cyanide (1.96 g, 7.30 mmol) in dry acetonitrile (40.0 ml) under nitrogen was heated under reflux for 24 h. The cooled solution was evaporated to yield an orange/brown oil which was taken up in ethyl acetate (200 ml), washed with water (3×100 ml), dried (Na$_2$SO$_4$) and the solvent removed in vacuo. Column chromatography (ethyl acetate—light petroleum (b.p. 40°–60° C.), 1:4) gave the title compound as a pale yellow oil (1.60 g, 74%). $[\alpha]_D^{19}$ −129 (c=0.005 gml$^{-1}$, CHCl$_3$); $\nu_{max}$ (thin film)/cm$^{-1}$ 3064, 3033, 2932, 2872, 2247 (CN), 1575; $\delta_H$ (270 MHz) 2.10 (2H, m, 2×propyl 3-H); 2.38 (2H, m, 2×propyl 2-H); 5.09 (2H, q, C$\underline{H}_2$Ph, $^2J$=10.9 Hz); 6.39 (1H, dd, propyl 1-H, $^3J_{1,2}$=9.7, $^3J_{1,2'}$=5.8 Hz); 6.55 (1H, d, 3-H, $^3J_{3,2}$=3.3 Hz); 6.70 (1H, d, 6-H, J$_o$=7.6 Hz); 6.83 (1H, d, 4-H, J$_o$=7.6 Hz); 7.00 (2H, m, 5-H, 5'-H); 7.05 (1H, d, 2-H, $^3J_{2,3}$=3.0 Hz); 7.15 (1H, s, 2'-H); 7.21 (1H, d, 6'-H, J$_o$=8.0 Hz); 7.30 (1H, d, 4'-H, J$_o$=8.6 Hz); 7.38 (5H, m, 5ArH).

(c) (1R)-(−)-1-[1-(3-Bromophenyl)-3-cyanopropyl]-7-cyanomethoxyindole. General procedure for the debenzylation and subsequent cyanomethylation of 7-benzyloxyindoles.

A 1.0M solution of boron tribromide in dichloromethane (13.0 ml, 13.0 nmol) was added dropwise over 20 min to a solution of (1R)-(−)-7-benzyloxy-1-[1-(3-bromophenyl)-3-cyanopropyl]indole (1.60 g, 3.59 mmol) in dichloromethane (40.0 ml) at −75° C. under nitrogen. The resulting orange/brown solution was stirred below −70° C. for an additional 5 min, quenched with 2M aqueous hydrochloric acid (200 ml) and extracted with dichloromethane (3×200 ml). The combined organic extracts were washed with 2M hydrochloric (200 ml), dried ($Na_2SO_4$) and the solvent removed in vacuo to yield a dark brown oil. This oil was dissolved in butanone (40.0 ml) and added dropwise to a stirred refluxing solution of bromoacetonitrile (1.30 ml, 17.96 mmol) and anhydrous potassium carbonate (13.6 g, 98.4 mmol) under nitrogen. The brown mixture was heated under reflux for 30 min, cooled to room temperature, filtered and the residue was washed with ethyl acetate (200 ml). The organic washings were combined, washed with water (2×200 ml), dried ($Na_2SO_4$) and adsorbed onto a quantity of silica (ca. 6.0 g). Column chromatography (ethyl acetate—light petroleum (b.p. 40°–60° C.), 1:4) gave the title compound as a pale yellow oil (1.00 g, 71%). $C_{20}H_{16}BrN_3O$ requires C, 60.93; H, 4.10; N, 10.66; Br, 20.27%); $[\alpha]_D^{28}$ −164 (c=0.009 gml$^{-1}$, CHCl$_3$); $\nu_{max}$ (thin film)/cm$^{-1}$ 3023.5, 2934.0, 2247.0 (CN), 1594.0, 576.0; $\delta_H$ (270 MHz) 2.34 (2H, m, 2×propyl 3-H); 2.51 (2H, m, 2×propyl 2-H); 4.85 (2H, dd, OC$\underline{H}_2$CN, $^2J$=15.2 Hz); 6.36 (1H, t, propyl 1-H, $^3J_{1,2}$=7.6 Hz); 6.58 (1H, d, Indole 3-H, $^3J_{3,2}$=2.3 Hz); 6.72 (1H, d, Indole 6-H, $J_o$ =7.6 Hz); 7.01–7.41 (7H, m, 7ArH); $\delta_C$ (67.8 MHz) 14.7 (Propyl 2-C), 31.1 (Propyl 3-C), 53.6 (OC$\underline{H}_2$CN), 58.7 (Propyl 1-C), 104.3 (Indole 3-C), 104.7 (Indole 6-C), 115.1 (CN), 116.4 (Indole 4-C), 118.7 (CN), 120.4 (Indole 5-C), 123.0 (3'-C), 125.3 (Indole 2-C), 128.2 (6'-C), 129.0 (Indole 3a-C), 129.5 (5'-C), 130.6 (4'-C), 131.3 (2'-C), 131.5 (1'-C), 142.4 (Indole 7a-C), 144.0 (Indole 7-C); m/z 409.2, 407.3 (2.36, 2.54, M$^+$), 341.1, 339.1 (1.04, 1.06), 329.3 (1.68), 238.0, 236.0 (1.20, 1.30), 195.2 (8.62), 172.1 (5.39), 171.0, 169.0 (1.59, 2,72), 132.1 (6.14), 116.1 (6.12), 43.0 (100).

(d) Trans-(1R)-(−)-7-chloro-2-(2-{3-[1-(7-cyanomethoxyindol-1-yl)-3-cyanopropyl]phenyl}ethenyl)quinoline A solution of (1R)-(−)-1-[1-(3-bromophenyl)-3-cyanopropyl]-7-cyanomethoxyindole (0.96 g, 2.44 mmol) and 7-chloro-2-ethenylquinoline (0.51 mg, 2.69 mmol) in acetonitrile (4.0 ml) and triethylamine (4.0 ml) was placed in a 10.0 ml capped bottle equipped with a pea stirrer. After degassing and flushing with nitrogen, bisdiphenylphosphinopropane palladium dichloride (60 mg, 122 μmol) was added in one portion and the mixture was heated at 100° C. for 4 days. The cooled reaction mixture was adsorbed onto a quantity of silica (ca. 4.0 g) and column chromatography (ethyl acetate—light petroleum (b.p. 40°–60° C.), 1:4) gave unreacted aryl bromide as an orange oil (0.21 g, 22%). Further elution gave the title compound as a grey/green oil (400 mg, 33%). $[\alpha]_D^{19}$ −159 (c=0.005 gml$^{-1}$, CHCl$_3$); $\nu_{max}$ (thin film)/cm$^{-1}$ 2246.0, 1652.5, 1607.0, 1575.5, 1520.5;

(e) Trans-(1R)-(−)-7-chloro-2-(2-{3-[1-(7-{1H-tetrazol-5-ylmethoxy}indol-1-yl)-3-(1H-tetrazol-5-yl) propyl]phenyl}ethenyl)quinoline A magnetically stirred solution of (1R)-(−)-7-chloro-2-(2-{3-[1-(7-cyanomethoxyindol-1-yl)-3-cyanopropyl]phenyl}ethenyl)quinoline (20) (0.30 g, 0.597 mmol) and tributyltin azide (0.79 g, 2.39 mmol) in 1,2-dimethoxyethane (5.0 ml) was heated at 150° C. for 5 h during which time the DME solvent was allowed to boil off. The resulting dark brown mass was allowed to cool to room temperature, dissolved in 10% acetic acid in methanol (15.0 ml) and evaporated in vacuo to give a dark red oil. The red oil was dissolved in aqueous 2M NaOH$_{(aq)}$ (100 ml), washed with dichloromethane (2×70.0 ml), ethyl acetate (2×70.0 ml) and light petroleum (b.p. 40°–60° C.) (3×70.0 ml). Acidification of the aqueous phase with acetic acid yielded the title compound (70%) as an olive green solid which was collected by filtration. $\nu_{max}$(thin film)/cm$^{-1}$ 3400 (br. OH), 1653.0, 1635.0, 1608.5, 1575.5; $\delta_H$ (270 MHz) 2.35 (2H, m, 2×propyl 1-H), 2.64 (2H, m, 2×propyl 2-H); 4.90 (2H, s, OC$\underline{H}_2$CN); 6.47 (1H, m, propyl 3-H); 6.61 (1H, m, indole 3-H); 6.75 (1H, m, indole 6-H); 7.03–7.70 (12H, m, 12×ArH); 8.06 (2H, m, quinoline 4-H, 8-H). $\delta_C$ (67.8 MHz) 14.7 (propyl 2-C), 31.2 (propyl 1-C), 53.6 (OC$\underline{H}_2$CN), 59.1 (propyl 3-C), 104.0 (indole 3-C), 104.6 (indole 6-C), 115.2 (CN), 116.3 (indole 4-C), 118.8 (CN), 119.7 (quinoline 3-C), 120.2 (indole 5-C), 140.6 (indole 7a-C), 144.1 (indole 7-C), 148.5 (quinoline 8a-C), 156.6 (quinoline 2-C). The remaining signals lie between 125.6 and 137.1 ppm and cannot be assigned with any certainty.

We claim:

1. A process for producing a compound of the formula (I)

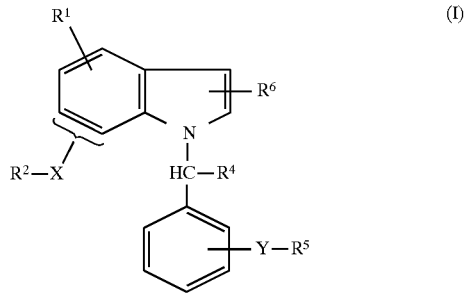

in which $R^1$ is hydrogen, halo, $C_{1-4}$ alkyl, $C_{1-4}$ alkoxy, nitrile, optionally protected carboxy, optionally protected tetrazolyl, trihalomethyl, hydroxy-$C_{1-4}$ alkyl, aldehyde, —CH$_2$Z, —CH=CH—Z or —CH$_2$CH$_2$Z where Z is optionally protected carboxy or optionally protected tetrazolyl; $R^2$ is halo, nitrile, an optionally protected acid group or —CONR$^7$R$^8$ where R$^7$ and R$^8$ are hydrogen or $C_{1-4}$ alkyl; $R^4$ is $C_{2-4}$ alkyl, or $C_{2-4}$ alkyl substituted by —CONR$^7$R$^8$ or an optionally protected acid group; $R^5$ is

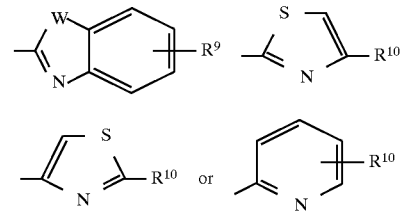

where W is —CH=CH—, —CH=N—, —N=CH—, —O— or —S—, $R^9$ is hydrogen, halo, $C_{1-4}$ alkyl, $C_{1-4}$ alkoxy or trihalomethyl, and $R^{10}$ is hydrogen, $C_{1-4}$ alkyl, $C_{2-6}$ alkenyl, $C_{3-6}$ cycloalkyl or $C_{1-4}$ alkyl-$C_{3-6}$ cycloalkyl; $R^6$ is hydrogen or $C_{1-4}$ alkyl; X is —O—(CH$_2$)$_n$CR$^{11}$R$^{12}$—, —CR$^{11}$R$^{12}$—, (CH$_2$)$_n$CR$^{13}$R$^{14}$— or —CR$^{11}$=CR$^{12}$— where $R^{11}$, $R^{12}$, $R^{13}$ and $R^{14}$ are each hydrogen or $C_{1-4}$ alkyl, and n is 0, 1 or 2; and Y is —O—CR$^{15}$R$^{16}$—, —CR$^{15}$=CR$^{16}$— or —CR$^{15}$R$^{16}$— where $R^{15}$ and $R^{16}$ are each hydrogen or $C^{1-4}$ alkyl; or a salt thereof, comprising the step of reacting a compound of the formula (II)

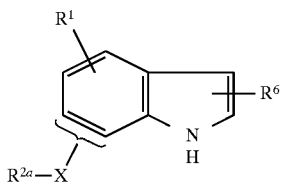

with a compound of the formula (III)

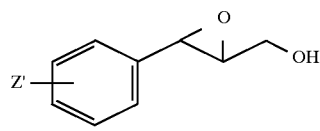

to form a compound of the formula (IV)

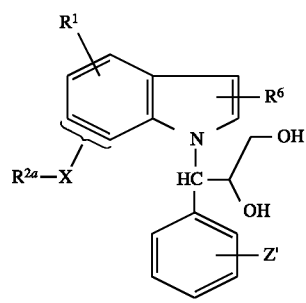

wherein $R^{2a}$ is selected from the groups recited above for $R^2$, or $R^{2a}$—X— is a protected hydroxyl group, and Z' is a group of formula —Y—$R^5$ recited above, or a group that can be converted into a group of said formula —Y—$R^5$; followed by converting the compound of formula (IV) to a compound of the formula (I).

2. A process according to claim 1, wherein Z' is a leaving group, an aldehyde group or a protected aldehyde group.

3. A process according to claim 2, wherein Z' is a leaving group suitable for a palladium catalyzed olefination reaction, said leaving group being selected from —Cl, —Br, —I, $CF_3SO_3$— and tosylate.

4. A process according to claim 1, including the further step of converting the compound of formula (IV) into a compound of the formula (IVa)

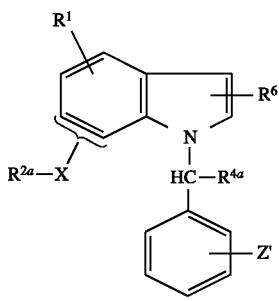

where $R^{4a}$ is $C_{2-4}$ alkyl, or $C_{2-4}$ alkyl substituted by cyano, hydroxy, —$CONR^7R^8$ or an optionally protected acid group.

5. A process according to claim 1, including the step of converting the compound of formula (IV) to the olefin (V)

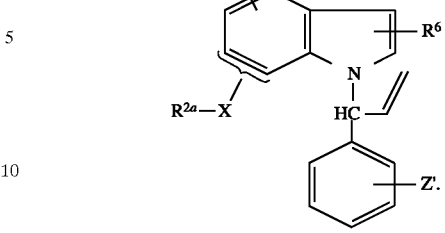

6. A process according to claim 5, including the further step of converting the compound of formula (V) to an indolene alcohol of the formula (VI):

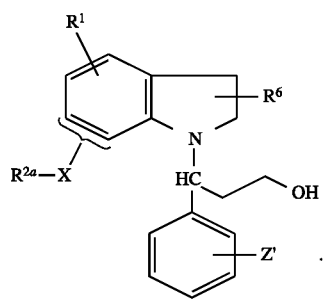

7. A process according to claim 6, including the further step of oxidizing the indoline alcohol of formula (VI) to an indole compound of the formula

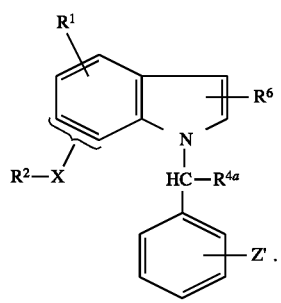

8. A process according to claim 7, further comprising the step of converting the compound of formula VII to form a compound of formula (IVa)

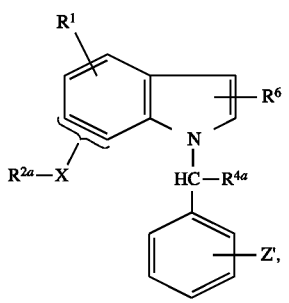

where $R^{4a}$ is $C_{2-4}$ alkyl or $C_{2-4}$ alkyl substituted by cyano, hydroxy, —$CONR^7R^8$ or an optionally protected acid group, said step comprising: (a) converting the hydroxyl group into a leaving group, followed by (b) reaction with a suitable nucleophile to produce the desired group $R^{4a}$.

9. A process according to claim 8, wherein step (b) comprises reaction with cyanide ions, or cyanomethylation with $NCCH_2CO_2H$ and lithium diisopropylamide, or with $CH_3CN$ and lithium diisopropylamide, in aprotic solvent.

10. A process according to claim 4 wherein $R^{2a}$—X— is a protected hydroxy group, comprising the step of removing the protecting group $R^{2a}$ from the compound of formula (IVa) and then reacting the deprotected compound with a compound of the formula Br—$(CH_2)_n CR^{11}R^{12}$—$R^2$ wherein n is 0, 1 or 2; and $R^{11}$ and $R^{12}$ are each hydrogen or $C_{1-4}$ alkyl, to form a compound of the formula (VIII)

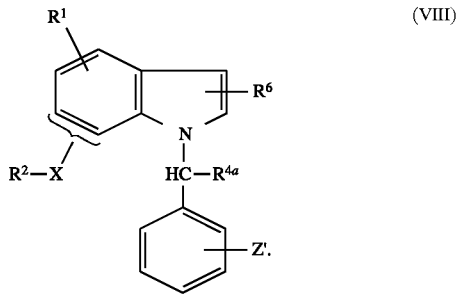

(VIII)

11. A process according to claim 4, wherein Y is —$CR^{15}$=$CR^{16}$— and Z is a leaving group, comprising the further step of reacting the compound of formula (IVa) with a compound of the formula $CHR^{15}$=$CR^{16}$—$R^5$ in the presence of a palladium salt, a polar solvent, a base and a monodentate or bidentate phosphine ligand to form a compound of the formula (IX)

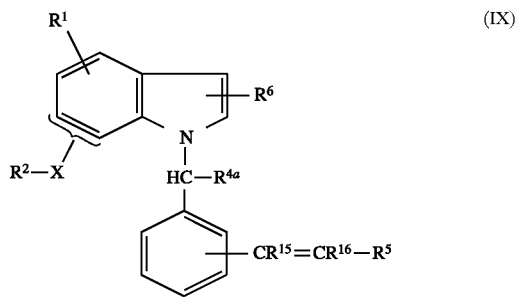

(IX)

in which $R^1$ is hydrogen, halo, $C_{1-4}$ alkyl $C_{1-4}$ alkoxy, nitrile, optionally protected carboxy, optionally protected tetrazolyl, trihalomethyl, hydroxy-$C_{1-4}$ alkyl aldehyde, —$CH_2Z$, —CH=CH—Z or —$CH_2CH_2Z$ where Z is optionally protected carboxy or optionally protected tetrazolyl; $R^2$ is halo, nitrile, an optionally protected acid group or —$CONR^7R^8$ where $R^7$ and $R^8$ are hydrogen or $C_{1-4}$ alkyl; $R^4$ is $C_{2-4}$ alkyl, or $C_{2-4}$ alkyl substituted by —$CONR^7R^8$ or an optionally protected acid group; $R^5$ is

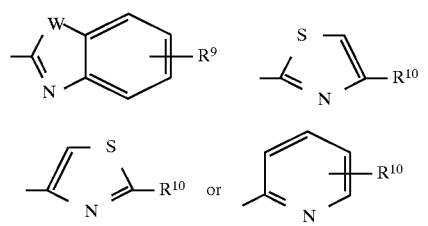

where W is —CH=CH—, —CH=N—, —N=CH—, —O— or —S—, $R^9$ is hydrogen, halo, $C_{1-4}$ alkyl, $C_{1-4}$ alkoxy or trihalomethyl, and $R^{10}$ is hydrogen, $C_{1-4}$ alkyl, $C_{2-6}$ alkenyl, $C_{3-6}$ cycloalkyl or $C_{1-4}$ alkyl-$C_{3-6}$ cycloalkyl; $R^6$ is hydrogen or $C_{1-4}$ alkyl; X is —O—$(CH_2)_n CR^{11}R^{12}$—, —$CR^{11}R^{12}$—, $(CH_2)_n$—$CR^{13}R^{14}$— or —$CR^{11}$=$CR^{12}$— where $R^{11}$, $R^{12}$, $R^{13}$ and $R^{14}$ are each hydrogen or $C_{1-4}$ alkyl and n is 0, 1 or 2; and Y is —O—$CR^{15}R^{16}$—, —$CR^{15}$=$CR^{16}$— or —$CR^{15}R^{16}$, where $R^{15}$ and $R^{16}$ are each hydrogen or $C_{1-4}$ alkyl; or a salt thereof.

12. A process according to claim 11 wherein $R^2$ in formula (IX) is cyano and/or $R^{4a}$ is cyano-$C_{2-4}$ alkyl, and the compound of formula (IX) is reacted with an azide to convert the cyano groups to tetrazolyl groups.

13. A process according to claim 1, wherein the epoxide compound of formula (III) is formed by reacting a compound of the formula

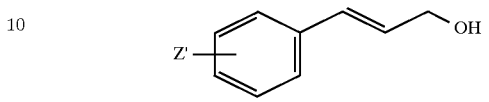

with a titanium alkoxide, an organic hydroperoxide and a chiral glycol in an aprotic solvent.

14. A process according to claim 13 wherein the chiral glycol is L-(+)-diethyl tartrate, such that the compound of formula (III) has the structure

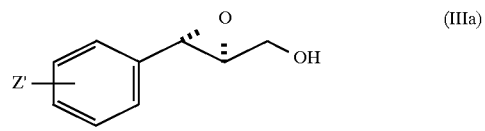

(IIIa)

and the resulting compound of formula (I) has the structure

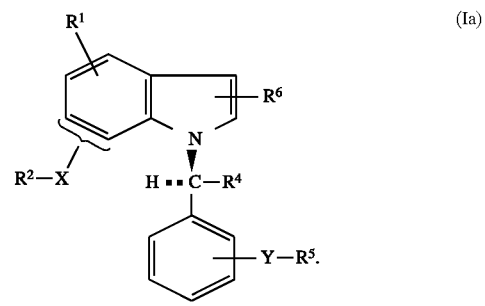

(Ia)

15. A process according to claim 13 wherein the chiral glycol is D-(−)-diethyl tartrate, such that the compound of formula (III) has the structure

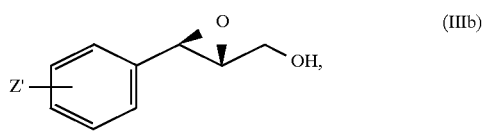

(IIIb)

and the resulting compound of formula (I) has the structure

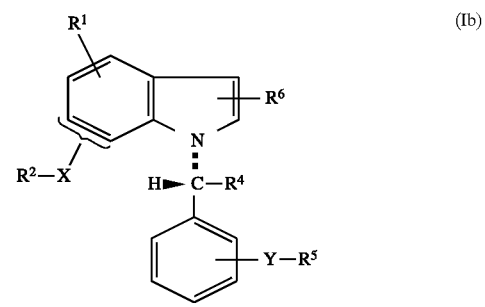

(Ib)

16. The process of claim 13, wherein the compound produced is (I')

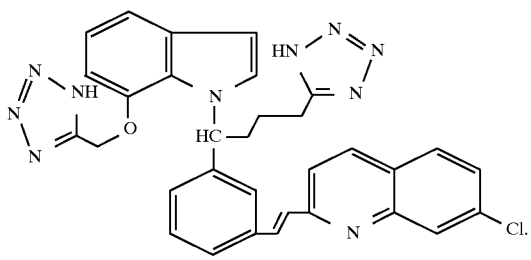 (I')

17. The process of claim 14 wherein the compound prepared is (1S)-(+)-7-chloro-2-(2-{3-[1-(7-{1H-tetrazol-5-ylmethoxy}indol-1-yl)-4-(1H-tetrazol-5-yl)butyl]phenyl}ethenyl)quinoline.

18. The process of claim 15 wherein the compound prepared is (1R)-(−)-7-chloro-2-(2-{3-[1-(7-{1H-tetrazol-5-ylmethoxy}indol-1-yl)-4-(1H-tetrazol-5-yl)butyl]phenyl}ethenyl)quinoline.

19. A process for producing a compound of the formula (IV)

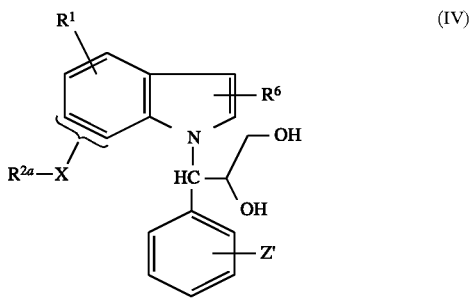 (IV)

wherein $R^1$ is hydrogen, halo, $C_{1-4}$ alkyl, $C_{1-4}$ alkoxy, nitrile, optionally protected carboxy, optionally protected tetrazolyl, trihalomethyl, hydroxy-$C_{1-4}$ alkyl, aldehyde, —CH$_2$Z, —CH=CH—Z or —CH$_2$CH$_2$Z where Z is optionally protected carboxy or optionally protected tetrazolyl; $R^{2a}$ is halo, nitrile, an optionally protected acid group or —CONR$^7$R$^8$ where $R^7$ and $R^8$ are hydrogen or $C_{1-4}$ alkyl, or $R^{2a}$—X— is a protected hydroxyl group; and Z' is a group of formula —Y—R$^5$, or a group that can be converted into a group of said formula —Y—R$^5$ in which R$^5$ is

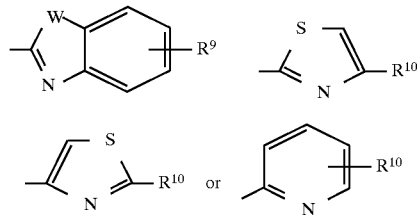

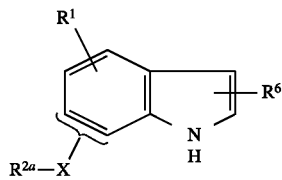 or 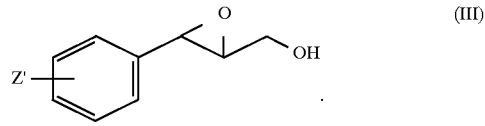

where W is —CH=CH—, —CH=N—, —N=CH—, —O— or —S—, $R^9$ is hydrogen, halo, $C_{1-4}$ alkyl, $C_{1-4}$ alkoxy or trihalomethyl, and $R^{10}$ is hydrogen, $C_{1-4}$ alkyl, $C_{2-6}$ alkenyl, $C_{3-6}$ cycloalkyl or $C_{1-4}$ alkyl-$C_{3-6}$ cycloalkyl; $R^6$ is hydrogen or $C_{1-4}$ alkyl; X is —O—(CH$_2$)$_n$CR$^{11}$R$^{12}$—, —CR$^{11}$R$^{12}$—, (CH$_2$)n—(CR$^{13}$R$^{14}$— or —CR$^{11}$=CR$^{12}$— where $R^{11}$, $R^{12}$, $R^{13}$ and $R^{14}$ are each hydrogen or $C_{1-4}$ alkyl, and n is 0, 1 or 2; and Y is —O—CR$^{15}$R$^{16}$—, —CR$^{15}$=CR$^{16}$— or —CR$^{15}$R$^{16}$ where $R^{15}$ and $R^{16}$ are each hydrogen or $C_{1-4}$ alkyl; or a salt thereof, comprising the step of reacting a compound of the formula (II)

(II)

with a compound of the formula (III)

(III)

* * * * *